United States Patent [19]

Bradshaw et al.

[11] Patent Number: 5,356,893
[45] Date of Patent: Oct. 18, 1994

[54] BENZANILIDE DERIVATIVES

[75] Inventors: John Bradshaw; John W. Clitherow; Ian B. Campbell, all of Ware, Great Britain

[73] Assignee: Glaxo Group Limited, London, England

[21] Appl. No.: 945,878

[22] Filed: Sep. 17, 1992

[30] Foreign Application Priority Data

Sep. 18, 1991 [GB] United Kingdom ............. 9119920.8

[51] Int. Cl.$^5$ ............... A61K 31/535; A61K 31/495; C07D 417/12; C07D 295/135

[52] U.S. Cl. ........................... 514/227.2; 514/227.8; 514/235.8; 514/252; 514/255; 544/54; 544/59; 544/60; 544/106; 544/121; 544/176; 544/229; 544/359; 544/360; 544/364; 544/365; 544/372; 544/374; 544/393; 544/395; 548/131; 548/539; 548/953; 558/49; 558/52; 558/54; 556/402; 560/30; 560/41; 560/103; 562/442; 564/90; 564/183; 564/366; 568/6; 568/337; 568/607; 568/812; 570/182

[58] Field of Search ................. 544/60, 121, 359, 360, 544/365, 372, 393, 54, 364, 374; 514/210, 227.8, 235.8, 252, 255, 227.2

[56] References Cited

U.S. PATENT DOCUMENTS

| | | | |
|---|---|---|---|
| 3,192,213 | 6/1965 | Krapcho | 564/182 |
| 4,058,523 | 11/1977 | Mori et al. | 544/165 |
| 4,116,960 | 9/1978 | Sellstedt et al. | 544/366 |
| 4,735,959 | 4/1988 | Grell et al. | 514/357 |

FOREIGN PATENT DOCUMENTS

| | | |
|---|---|---|
| 86/67002 | 7/1987 | Australia . |
| 0058779 | 9/1982 | European Pat. Off. . |
| 0210782 | 2/1987 | European Pat. Off. . |
| 0310370 | 4/1989 | European Pat. Off. . |
| 0324521 | 7/1989 | European Pat. Off. . |
| 0365064 | 4/1990 | European Pat. Off. . |
| 2545978 | 4/1976 | Fed. Rep. of Germany . |
| 1157586 | 7/1984 | United Kingdom . |

84/00545 2/1984 World Int. Prop. O. .

OTHER PUBLICATIONS

Charles et al., *Archiv der Pharmazie*, 315, No. 2, pp. 97-103, Feb., 1982.
Abstract for JP 63-258446 (Oct. 25, 1988).

*Primary Examiner*—Emily Bernhardt
*Attorney, Agent, or Firm*—Bacon & Thomas

[57] ABSTRACT

The invention provides compounds of formula (I):

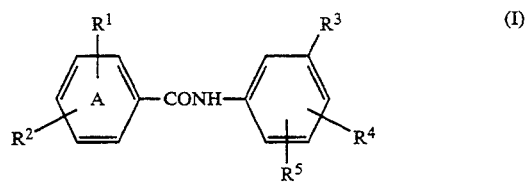

or a physiologically acceptable salt or solvate thereof wherein $R^1$ represents a halogen or hydrogen atom or a $C_{1-6}$alkyl or $C_{1-6}$alkoxy group;

$R^2$ represents a phenyl group optionally substituted by one or two substituents;

$R^3$ represents the group

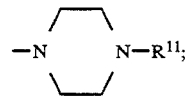

$R^4$ and $R^5$, which may be the same or different, each independently represent a hydrogen atom or a halogen atom, or a group selected from hydroxy, $C_{1-6}$alkoxy or $C_{1-6}$alkyl.

The compounds may be used in the treatment or prophylaxis of depression and other CNS disorders.

22 Claims, No Drawings

BENZANILIDE DERIVATIVES

This invention relates to novel benzanilide derivatives, to processes for their preparation, and to pharmaceutical compositions containing them.

According to the invention we provide compounds of the general formula (I):

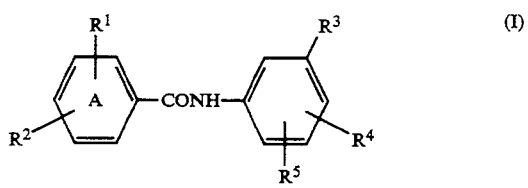

or a physiologically acceptable salt or solvate (e.g. hydrate) thereof, in which $R^1$ represents a halogen or hydrogen atom or a $C_{1-6}$alkyl or $C_{1-6}$alkoxy group;

$R^2$ represents a phenyl group optionally substituted by one or two substituents selected from a halogen atom, $C_{1-6}$alkyl, hydroxy$C_{1-6}$alkyl, $C_{1-6}$alkoxy, hydroxy, —$CF_3$, —CN, —$NO_2$, —$CO_2R^{10}$, —$COR^6$, —$SR^6$, —$SOR^6$, —$SO_2R^6$, —$CR^6$=$NOR^7$, —$CONR^6R^7$, —$CONR^6(CH_2)_mCO_2R^7$, —$CONR^6(CH_2)_mOC_{1-4}$alkyl, —$SO_2NR^6R^7$, —$OC(O)NR^6R^7$, —$(CH_2)_nNR^8R^9$, —$(CH_2)_nOC(O)C_{1-4}$alkyl or a $C_{1-4}$alkoxyalkyl group optionally substituted by a $C_{1-4}$alkoxy or hydroxy group;

$R^3$ represents the group

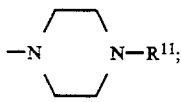

$R^4$ and $R^5$, which may be the same or different each independently represent a hydrogen atom or a halogen atom, or a group selected from hydroxy, $C_{1-6}$alkoxy or $C_{1-6}$alkyl;

$R^6$, $R^7$ and $R^8$, which may be the same or different, each independently represent a hydrogen atom or a $C_{1-6}$alkyl group;

or —$NR^6R^7$ forms a saturated heterocyclic ring which has 4, 5 or 6 ring members which, when there are 6 ring members, may optionally contain in the ring one oxygen or sulphur atom;

$R^9$ represents a hydrogen atom or a group selected from $C_{1-6}$alkyl, —$COR^{12}$ or —$SO_2R^{13}$;

or —$NR^8R^9$ forms a saturated heterocyclic ring which has 5 or 6 ring members, may optionally be substituted by an oxo group and, when there are 6 ring members, may optionally contain in the ring one oxygen or sulphur atom;

$R^{10}$ represents a hydrogen atom or a $C_{1-6}$alkyl group optionally substituted by one or two substituents selected from a $C_{1-6}$alkyl group, $C_{1-6}$alkoxy group, hydroxy or —$NR^6R^7$;

$R^{11}$ represents a hydrogen atom or a $C_{1-6}$alkyl group;

$R^{12}$ represents a hydrogen atom or a group selected from $C_{1-6}$alkyl, $C_{1-6}$alkoxy or a $C_{1-4}$alkoxyalkyl group;

$R^{13}$ represents a $C_{1-6}$alkyl or phenyl group;

m represents an integer from 1 to 3; and n represents zero or an integer from 1 to 3.

It is to be understood that the present invention encompasses all geometric and optical isomers of the compounds of general formula (I) and their mixtures including the racemic mixtures thereof.

Physiologically acceptable salts of the compounds of formula (I) include acid addition salts formed with inorganic or organic acids (for example hydrochlorides, hydrobromides, sulphates, phosphates, benzoates, naphthoates, hydroxynaphthoates, p-toluenesulphonates, methanesulphonates, sulphamates, ascorbates, tartrates, citrates, oxalates, maleates, salicylates, fumarates, succinates, lactates, glutarates, gluconates, acetates or tricarballylates) and, where appropriate, inorganic base salts such as alkali metal salts (for example sodium salts).

In the compounds of formula (I), the term '$C_{1-6}$alkyl' or '$C_{1-6}$alkoxy' as a group or part of a group means that the group is straight or branched and consists of 1 to 6 carbon atoms. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy. The term 'halogen' within the definition of $R^2$ means fluorine, chlorine, bromine or iodine.

Within the above definition, when —$NR^6R^7$ or —$NR^8R^9$ represent a saturated heterocyclic ring, these contain 5 or 6 ring members, one of which (when there are 6 ring members) may be an oxygen or a sulphur atom. Suitable heterocyclic groups are a pyrrolidino, piperidino, morpholino or thiomorpholino group.

where a saturated heterocyclic ring is formed by the group —$NR^8R^9$ and said ring is substituted by an oxo group, suitable heterocyclic groups include a 2-oxo-1-pyrrolidino, 4-oxo-3-thaizolidino or 2-oxo-tetrahydro-1,3-thiazino group.

The group $R^2$ may preferably be attached in the meta or more particularly the para position of the benzene ring A relative to the amide linkage.

When the phenyl group of $R^2$ is substituted by a single atom or group as defined above the substituent is preferably attached in a position meta or para to the phenyl ring A in general formula (I). When the phenyl group of $R^2$ is substituted by two atoms or groups as defined above one substituent is preferably attached in the position para to, and the other is in a position ortho to the bond to the phenyl ring A in general formula (I).

A preferred group of compounds of general formula (I) is that wherein $R^2$ represents a phenyl group substituted by one or two substituents as defined in general formula (I) wherein one substituent is in the position para to the bond to the phenyl ring A in general formula (I) and the second substituent is in the position ortho to the bond to the phenyl ring A in general formula (I).

Another preferred group of compounds of general formula (I) is that wherein $R^2$ represents a phenyl group substituted by a single substituent as defined in general formula (I) wherein said substituent is in the position para to the bond to the phenyl ring A in general formula (I).

A further preferred group of compounds of general formula (I) is that wherein $R^2$ represents a phenyl group optionally substituted by one or two substituents selected from a halogen atom; or a $C_{1-6}$alkyl, especially methyl, group; hydroxymethyl; hydroxy; —CN; —$COR^6$ where $R^6$ is a $C_{1-6}$alkyl especially methyl, ethyl, propyl or butyl, group; —$SR^6$ where $R^6$ is a $C_{1-6}$alkyl especially methyl, group; —$SOR^6$ where $R^6$ is a $C_{1-6}$alkyl, especially methyl, group; —$CR^6$=$NOR^7$ where $R^6$ is a hydrogen atom or a $C_{1-6}$alkyl, especially methyl, group, and $R^7$ is a hydrogen atom or a $C_{1-6}$alkyl especially, methyl, group; —CONR$^6$R$^7$ where $R^6$ and $R^7$ each independently represent $C_{1-6}$alkyl, especially methyl, groups or —NR$^6$R$^7$ forms a saturated heterocyclic group which has six members and contains in the ring one oxygen atom, especially a morpholino ring; —CONR$^6$(CH$_2$)$_n$OC$_{1-4}$alkyl, where $R^6$ is a $C_{1-6}$alkyl, especially methyl group and n is two, especially the group —CON(CH$_3$)(CH$_2$)$_2$OCH$_3$; —SO$_2$NR$^6$R$^7$ where $R^6$ and $R^7$ each independently represent a hydrogen atom or a $C_{1-6}$alkyl, especially methyl, group; —OC(O)NR$^6$R$^7$ where $R^6$ and $R^7$ each independently represent a $C_{1-6}$alkyl, especially methyl, group; —(CH$_2$)$_n$NR$^8$R$^9$ where $R^8$ is a hydrogen atom or a $C_{1-6}$alkyl, especially methyl, group, $R^9$ is a $C_{1-6}$alkyl, especially methyl, group, or —COR$^{12}$ (where $R^{12}$ is a $C_{1-6}$alkyl, especially methyl, group, a $C_{1-6}$alkoxy, especially methoxy or ethoxy, group or a $C_{1-4}$alkoxyalkyl, especially methoxymethyl, group) or —SO$_2$R$^{13}$ (where $R^{13}$ is a $C_{1-6}$alkyl, especially methyl, group), or —NR$^8$R$^9$ forms a saturated heterocyclic group which has six ring members and contains in the ring one oxygen or sulphur atom, especially a morpholino or thiomorpholino ring, and n is zero, 1 or 2; or a $C_{1-4}$alkoxyalkyl, especially methoxymethyl or methoxyethyl, group substituted by a $C_{1-4}$alkoxy, especially methoxy, group.

Another preferred group of compounds of general formula (I) is that wherein $R^2$ represents a phenyl group substituted by a group selected from hydroxymethyl, hydroxy, —COCH$_3$, —SOCH$_3$, —C(CH$_3$)=NOH, —CON(CH$_3$)$_2$, —SO$_2$NH$_2$, —SO$_2$NHCH$_3$, —SO$_2$N(CH$_3$)$_2$, —OC(O)N(CH$_3$)$_2$, —NHCH$_3$, —N(CH$_3$)$_2$, —N(CH$_3$)COCH$_3$, —CH$_2$NHCO$_2$CH$_2$CH$_3$, —CH$_2$N(CH$_3$)COCH$_2$OCH$_3$, —NHSO$_2$CH$_3$,

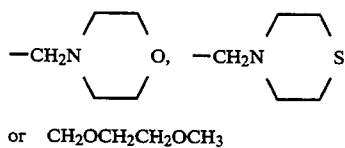

or CH$_2$OCH$_2$CH$_2$OCH$_3$ and optionally further substituted by a chlorine atom or a methyl group.

Also preferred is the group of compounds of general formula (I) wherein $R^1$ is a hydrogen atom or a $C_{1-6}$alkyl, especially methyl, group.

Another preferred group of compounds of general formula (I) is that wherein $R^4$ is attached in the para-position relative to the amide linkage.

A further preferred group of compounds of general formula (I) is that wherein $R^4$ is a halogen atom, especially a fluorine or chlorine atom, or a hydroxy or $C_{1-6}$alkoxy, especially methoxy, group.

Also preferred is the group of compounds of general formula (I) wherein $R^5$ is a hydrogen atom.

Further preferred is the group of compounds of general formula (I) wherein $R^5$ is a halogen atom, especially a chlorine or fluorine atom.

A yet further preferred group of compounds of general formula (I) is that wherein $R^{11}$ is a $C_{1-6}$alkyl, especially methyl, group.

Particularly preferred compounds of general formula (I) include:

N-[4-methoxy-3-(4-methyl-1-piperazinyl)phenyl]-2-methyl-4'-(methylsulphinyl)-[1,1'-biphenyl]-4-carboxamide;

4'-acetyl-N-[4-methoxy-3-(4-methyl-1-piperazinyl)phenyl]-2-methyl-[1,1'-biphenyl]-4-carboxamide;

N-[4-methoxy-3-(4-methyl-1-piperazinyl)phenyl]-2'-methyl-4'-methylamino-[1,1'-biphenyl]-4-carboxamide;

ethyl [4'-[[[4-methoxy-[3-(4-methyl-1-piperazinyl)]phenyl]amino]carbonyl]-2-methyl-([1,1'-biphenyl]-4-yl)]methyl carbamate;

4'-[[[4-methoxy-3-(4-methyl-1-piperazinyl)phenyl]amino]carbonyl]-2'-methyl-[1,1'-biphenyl]-4-dimethylcarbamate;

4'-[[(methoxyacetyl)methylamino]methyl]-N-[4-methoxy-3-(4-methyl-1-piperazinyl)phenyl]-2'-methyl-[1,1'-biphenyl]-4-carboxamide; and their physiologically acceptable salts and solvates.

Further preferred compounds of general formula (I) include:

4'-acetyl-2'-trifluoromethyl-N-[4-methoxy-3-(4-methyl-1-piperazinyl)phenyl]-[1,1'-biphenyl]-4-carboxamide;

N-[4-bromo-3-(4-methyl-1-piperazinyl)phenyl]-N',N',2'-trimethyl-[1,1'-biphenyl]-4,4'-dicarboxamide;

4'-hydroxy-N-[4-methoxy-3-(4-methyl-1-piperazinyl)phenyl]-[1,1'-biphenyl]-4-carboxamide;

4'-acetyl-N-[4-methoxy-3-(4-methyl-1-piperazinyl)phenyl]-2'-methyl-[1,1'-biphenyl]-4-carboxamide;

N-[4-methoxy-3-(4-methyl-1-piperazinyl)phenyl]-2'-methyl-4'-(4-morpholinylcarbonyl)-[1,1'-biphenyl]-4-carboxamide;

4'-acetyl-2'-methoxy-N-[4-methoxy-3-(4-methyl-1-piperazinyl)phenyl][1,1'-biphenyl]-4-carboxamide;

N-[4-methoxy-3-(4-methyl-1-piperazinyl)phenyl]-N',N'-dimethyl [1,1'-biphenyl]-4,4'-dicarboxamide;

N-[4-methoxy-3-(4-methyl-1-piperazinyl)phenyl]-2'methyl-4'-[(1-pyrrolidinyl)carbonyl][1,1'-biphenyl]-4-carboxamide;

N,N-diethyl-N-[4-methoxy-3-(4-methyl-1-piperazinyl)phenyl]-2-methyl[1,1'-biphenyl]-4,4'-dicarboxamide;

N-[4-methoxy-3-(4-methyl-1-piperazinyl)phenyl]-2'-methyl-4'-[(methylsulphonyl)amino]-[1,1'-biphenyl]-4-carboxamide;

N-butyl-N'-[4-methoxy-3-(4-methyl-1-piperazinyl)phenyl]-N,2-dimethyl[1,1'-biphenyl]-4,4'-dicarboxamide;

N-[4-methoxy-3-(4-methyl-1-piperazinyl)phenyl]-N',N'-dipropyl[1,1'-biphenyl]-4,4'-dicarboxamide;

and their physiologically acceptable salts and solvates.

Particularly preferred compounds of general formula (I) include:

4'-[(2-methoxyethoxy)methyl]-N-[4-methoxy-3-(4-methyl-1-piperazinyl)phenyl]-2'-methyl-[1,1'-biphenyl]-4-carboxamide;

4'-cyano-N-[4-methoxy-3-(4-methyl-1-piperazinyl)phenyl]-2'-methyl-[1,1'-biphenyl]-4-carboxamide;

N-[4-methoxy-3-(4-methyl-1-piperazinyl)phenyl]-N',N',2'-trimethyl-[1,1'-biphenyl]-4,4'-dicarboxamide;

4'-(dimethylamino)-N-[4-methoxy-3-(4-methyl-1-piperazinyl)phenyl]-2'-methyl-[1,1'-biphenyl]-4-carboxamide;

2-chloro-N'-[4-methoxy-3-(4-methyl-1-piperazinyl)phenyl]-N,N-dimethyl-[1,1'-biphenyl]-4,4'-dicarboxamide;

N-[4-chloro-3-(4-methyl-1-piperazinyl)phenyl]-N',N',2'-trimethyl-[1,1'-biphenyl]-4,4'-dicarboxamide;

N-(1,1-dimethylethyl)-N'-[4-methoxy-3-(4-methyl-1-piperazinyl)phenyl]-2-methyl[1,1'-biphenyl]-4,4'-dicarboxamide;

4'-[(1-azetidinyl)carbonyl]-N-[4-methoxy-3-(4-methyl-1-piperazinyl)phenyl]-2'-methyl[1,1'-biphenyl]-4-carboxamide;

and their physiologically acceptable salts and solvates.

5-Hydroxytryptamine (serotonin) is a neurotransmitter which is widely distributed within the central nervous system (CNS), platelets and the gastrointestinal tract. Changes in transmission in serotonergic pathways in the CNS are known to modify, for example, mood, psychomotor activity, appetite, memory and blood pressure. Release of 5-hydroxytryptamine from platelets can mediate vasospasm while changes in free 5-hydroxytryptamine levels in the gastrointestinal tract can modify secretion and motility.

Abundant pharmacological studies have led to the discovery of multiple types of receptors for 5-hydroxytryptamine, thus providing a molecular basis to the diversity of its actions. These receptors are classed as 5-HT$_1$, 5-HT$_2$ and 5-HT$_3$, with 5-HT$_1$ receptors being sub-classified as 5-HT$_{1A}$, 5-HT$_{1B}$, 5-HT$_{1C}$, 5-HT$_{1D}$ and 5-HT$_{1D}$(like) receptors. The identification of these classes and sub-classes of receptor is based mainly on radiological binding studies.

Compounds having a selective antagonist action at 5-HT$_{1D}$ receptors such as those described herein may exhibit a beneficial effect on subjects suffering from CNS disorders.

Accordingly, in a further aspect of the present invention, there is provided a method of treating a patient suffering from a CNS disorder, which method comprises administering to the patient an effective amount of a 5-HT$_{1D}$ antagonist. The patient is preferably a human patient.

In another aspect of the present invention, there is provided a 5-HT$_{1D}$ antagonist for use in the manufacture of a medicament for the treatment of a CNS disorder.

In the present specification, a 5-HT$_{1D}$ antagonist is a non-naturally occurring (synthetic) compound that specifically and selectively antagonises 5-HT$_{1D}$ receptors, i.e.—blocks the specific actions of 5-hydroxytryptamine mediated by the 5-HT$_{1D}$ receptor. Such compounds may be identified by a high level of affinity (pKi$\geq$8) in the in vitro human cortex and guinea-pig striatum radioligand binding assays described by Hoyer et al, Neuroscience Letters, 1988, 85, p357–362. Activity at 5-HT$_{1D}$ receptors may be confirmed in vivo using the guinea pig rotation model described by G A Higgins et al, Br. J. Pharmacol., 1991, 102, p305–310.

A 5-HT$_{1D}$ antagonist for use in the present method of treatment must be selective for 5-HT$_{1D}$ receptors. In the present specification, this means that the 5-HT$_{1D}$ antagonist must be 30 or more times more selective for 5-HT$_{1D}$ receptors than 5-HT$_{1A}$, 5-HT$_{1C}$ or 5-HT$_2$ receptors.

According to this definition the affinity of a compound for 5-HT$_{1A}$, 5-HT$_{1C}$ and/or 5-HT$_2$ receptors is measured using the in vitro tests described in the following publications:

5-HT$_{1A}$ Gozlan et al, Nature, 1983, 305, p 140–142

-continued

5-HT$_{1C}$ Pazos et al, Eur. J. Pharmacol., 1984, 106, p 531–538
5-HT$_2$ Humphrey et al, Br. J. Pharmacol, 1988, 94, p 1123–1132 (rabbit aorta model).

Thus, for example, compounds of the present invention have been shown to inhibit 5-hydroxytryptamine induced contraction of the dog isolated saphenous vein and to antagonise the 5-hydroxytryptamine induced inhibition of neurotransmission in central and peripheral neurones.

5-HT$_{1D}$ Antagonists, and in particular the compounds of the present invention, may therefore be of use in the treatment of CNS disorders such as mood disorders, including depression, seasonal affective disorder and dysthymia; anxiety disorders, including generalised anxiety, panic disorder, agoraphobia, social phobia, obsessive compulsive disorder and post-traumatic stress disorder; memory disorders, including dementia, amnestic disorders and age-associated memory impairment; and disorders of eating behaviour, including anorexia nervosa and bulimia nervosa. Other CNS disorders include Parkinson's disease, dementia in Parkinson's disease, neuroleptic-induced parkinsonism and tardive dyskinesias, as well as other psychiatric disorders.

5-HT$_{1D}$ Antagonists, and in particular compounds of the present invention, may also be of use in the treatment of endocrine disorders such as hyperprolactinaemia, the treatment of vasospasm (particularly in the cerebral vasculature) and hypertension, as well as disorders in the gastrointestinal tract where changes in motility and secretion are involved. They may also be of use in the treatment of sexual dysfunction.

Therefore, according to a second aspect of the invention, we provide a compound of general formula (I) or a physiologically acceptable salt or solvate thereof for use in therapy.

According to a further aspect of the present invention, we therefore provide a compound of general formula (I) or a physiologically acceptable salt or solvate thereof for use in the treatment of the aforementioned disorders.

According to another aspect of the invention, we provide the use of a compound of general formula (I) or a physiologically acceptable salt or solvate thereof for the manufacture of a therapeutic agent for the treatment of the aforementioned disorders.

According to a further aspect of the invention, we provide, a method of treating the aforementioned disorders which comprises administering an effective amount to a patient in need of such treatment of a compound of general formula (I) or a physiologically acceptable salt or solvate thereof.

In particular, according to another aspect of the present invention, we provide a compound of general formula (I) or a physiologically acceptable salt or solvate thereof for use in the treatment or prophylaxis of depression.

It will be appreciated that the compounds according to the invention may advantageously be used in conjunction with one or more other therapeutic agents, for instance, different antidepressant agents such as tricyclic antidepressants (e.g. amitriptyline, dothiepin, doxepin, trimipramine, butriptyline, clomipramine, desipramine, imipramine, iprindole, lofepramine, nortriptyline or protriptyline), monoamine oxidase inhibitors (e.g.

isocarboxazid, phenelzine or tranylcyclopramine) or 5-HT reuptake inhibitors (e.g. fluvoxamine, sertraline, fluoxetine or paroxetine), and/or antiparkinsonian agents such as dopaminergic antiparkinsonian agents (e.g. levodopa, preferably in combination with a peripheral decarboxylase inhibitor e.g. benserazide or carbidopa, or a dopamine agonist e.g. bromocriptine, lysuride or pergolide). It is to be understood that the present invention covers the use of a compound general formula (I) or a physiologically acceptable salt or solvate thereof in combination with one or more other therapeutic agents.

Thus there is provided in a further or alternative aspect of the present invention a compound of general formula (I) or a physiologically acceptable salt or solvate thereof and an antidepressant agent in the presence of each other in the human or non-human animal body for use in the treatment of the aforementioned disorders.

In a particular aspect of the present invention there is provided a compound of general formula (I) or a physiologically acceptable salt or solvate thereof and an antiparkinsonian agent such as a dopaminergic antiparkinsonian agent, e.g. levodopa, and a peripheral decarboxylase inhibitor, e.g. benserazide or carbidopa, or a dopamine agonist e.g. bromocriptine, lysuride or pergolide, in the presence of each other in the human or non-human animal body for use in the treatment of Parkinson's disease, dementia in parkinsonism, neuroleptic induced parkinsonism and tardive dyskinesias.

In using a compound of general formula (I) or a physiologically acceptable salt or solvate thereof and one or more therapeutic agents it may be preferable to employ the active ingredients in the form of separate pharmaceutical formulations. A combined formulation can be used, however, in such a combined formulation the active ingredients must of course be stable and mutually compatible in the particular formulation employed.

It will be appreciated that administration of the active ingredients to a human or non-human patient may be simultaneous, separate or sequential. Where administration is not simultaneous, the delay in administering the second of the active ingredients should not be such as to lose the beneficial effect of the combination.

While it is possible that a compound of general formula (I) may be administered as the raw chemical it is preferable to present the active ingredient as a pharmaceutical formulation.

The compounds of general formula (I) and their physiologically acceptable salts and solvates may be formulated for administration in any convenient way, and the invention therefore also includes within its scope pharmaceutical compositions comprising at least one compound of general formula (I) or a physiologically acceptable salt or solvate thereof. Such compositions may be presented for use in a conventional manner in admixture with one or more physiologically acceptable carriers or excipients.

The carrier(s) must be "acceptable" in the sense of being compatible with the other ingredients of the formulation and not deleterious to the recipient thereof.

Thus, the compositions according to the invention may be formulated for oral, buccal, parenteral or rectal administration or in a form suitable for administration by inhalation or insufflation. Oral administration is preferred.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcrystalline cellulose maize-starch, calcium phosphate or sorbitol; lubricants, for example, magnesium stearate, stearic acid, talc, polyethylene glycol or silica; disintegrants, for example, potato starch or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methylcellulose, glucose/sugar syrup, gelatin, hydroxypropyl methylcellulose, carboxymethylcellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by bolus injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation either orally or nasally the compositions according to the invention are conveniently delivered in the form of an aerosol spray presentation from pressurised packs with the use of a suitable propellant, e.g. dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation the compositions according to the invention may take the form of a dry powder composition, for example a powder mix of the compound and a suitable powder base such as lactose or starch. The powder composition may be presented in unit dosage form in, for example, capsules or cartridges of e.g. gelatin, or blister packs from which the powder may be administered with the aid of an inhaler or insufflator.

The pharmaceutical formulations according to the invention may also contain other active ingredients such as antimicrobial agents, or preservatives.

The compositions according to the invention may be prepared by mixing the various ingredients using conventional means.

It will be appreciated that the amount of a compound of general formula (I) required for use in treatment will vary not only with the particular compound selected but also with the route of administration, the nature of the condition being treated and the age and condition of the patient and will ultimately be at the discretion of the attendant physician or veterinarian. In general, however, a proposed dose of the compounds of the invention for administration in man is 0.5 to 1000 mg, preferably 1 to 200 mg of the active ingredient per unit dose which could be administered, for example, 1 to 4 times per day.

The compounds of the invention may be prepared by a number of processes as described in the following. In describing the processes which may be used for preparing the compounds of general formula (I) or intermediates useful in the preparation thereof, any of $R^1$–$R^{13}$, m and n in the various formulae are as defined in general formula (I) unless otherwise stated.

It will be appreciated that in the following methods for the preparation of compounds of general formula (I), for certain reaction steps it may be necessary to protect various reactive substituents in the starting materials for a particular reaction and subsequently to remove the protecting group. Such protection and subsequent deprotection may be particularly pertinent where $R^6$, $R^7$, $R^8$, $R^9$, $R^{10}$ and/or $R^{11}$ in intermediates used to prepare compounds of general formula (I) are hydrogen atoms. Standard protection and deprotection procedures can be employed, for example formation of a phthalimide (in the case of a primary amine), benzyl, trityl, benzyloxycarbonyl or trichloroethoxycarbonyl derivatives. Subsequent removal of the protecting group is achieved by conventional procedures. Thus a phthalimide group may be removed by treatment with hydrazine or a primary amine, for example methylamine. Benzyl or benzyloxycarbonyl groups may be removed by hydrogenolysis in the presence of a catalyst e.g. palladium, and trichloroethoxycarbonyl derivatives may be removed by treatment with zinc dust. Trityl groups may be removed under acidic conditions using standard procedures.

It may also be necessary in some cases to protect carboxylic acid groups (e.g. as esters) or aldehyde or ketone groups (e.g. as acyclic or cyclic acetals or ketals or as thioacetals or thioketals). Subsequent removal of these protecting groups is achieved by conventional procedures. Thus for example alkyl esters may be removed under conditions of acidic or basic hydrolysis, benzyl esters may be removed by hydrogenolysis in the presence of a catalyst e.g. palladium. Acyclic or cyclic acetals or ketals may be removed under conditions of acidic hydrolysis and thioacetals and thioketals may be removed using a mercuric salt.

Hydroxyl groups may also need protection and these may be adequately protected under amenable conditions as their esters or trialkylsilyl, tetrahydropyran and benzyl ethers. Such derivatives may be deprotected by standard procedures.

According to one general process (1), the compounds of general formula (I) may be prepared by a carbonylation reaction involving an aniline (II)

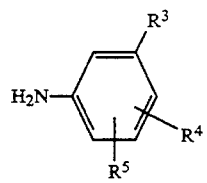

(where $R^3$, $R^4$ and $R^5$ are as defined in general formula (I)) and a halophenyl compound (III)

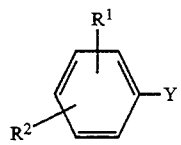

(where Y represents a halogen atom e.g. bromine or iodine or the group —$OSO_2CF_3$, and $R^1$ and $R^2$ are as defined in general formula (I)).

The reaction takes place, for example, in the presence of carbon monoxide using a palladium salt as a catalyst. The reaction is effected in the presence of a suitable base e.g. a trialkylamine such as triethylamine or tri-n-butylamine and may be conducted in a suitable solvent such as an amide e.g. dimethylformamide or a nitrile e.g. acetonitrile at a temperature within the range of $-10°$ C. to $+150°$ C.

Suitable palladium salts for the reaction include triarylphosphine palladium (II) salts such as bis(triphenylphosphine)palladium (II) chloride.

According to another general process (2), the compounds of general formula (I) may be prepared by treating a compound of formula (IV)

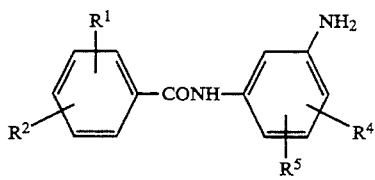

with an amine dihalide of formula (V)

$$R^{11}N(CH_2CH_2Hal)_2 \qquad (V)$$

(where Hal is a chlorine, bromine or iodine atom).

The reaction may conveniently take place in the presence of a polar solvent such as an alcohol (e.g. n-butanol) or a nitrile (e.g. acetonitrile), optionally in the presence of a base, for example, an alkali metal carbonate such as sodium carbonate or potassium carbonate, or alternatively in a non-polar solvent (e.g. chlorobenzene) in the absence of a base. The reactions may conveniently be carried out at an elevated temperature, for example, reflux.

According to another general process (3), the compounds of general formula (I) may be prepared by reacting an aniline of formula (II) with an activated carboxylic acid derivative of formula (VI)

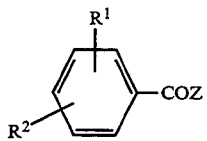

(VI)

(where Z is a leaving group).

Suitable activated carboxylic acid derivatives represented in formula (VI) include acyl halides (e.g. acid chlorides) and acid anhydrides including mixed anhydrides (e.g. acid formic anhydride). These activated derivatives may be formed from the corresponding acid of formula (VII)

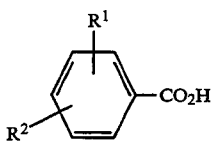

(VII)

by well known procedures. For example, acid chlorides may be prepared by reaction with phosphorus pentachloride, thionyl chloride or oxalyl chloride and acid anhydrides may be prepared by reaction with an appropriate acid anhydride (e.g. trifluoroacetic anhydride), an acid chloride (e.g. acetyl chloride), an alkyl or aralkyl haloformate (e.g. ethyl or benzyl chloroformate) or methanesulphonyl chloride.

Activated carboxylic acid derivatives of formula (VI) may also be prepared in situ by the reaction of the corresponding acids of formula (VII), with a coupling reagent such as carbonyldiimidazole, dicyclohexylcarbodiimide or diphenylphosphorylazide.

The conditions under which the activated carboxylic acid derivatives of formula (VI) are formed and subsequently reacted with the anilines of formula (II) will depend upon the nature of the activated derivative. However, in general the reaction between the compounds (II) and (VI) may be carried out in a non-aqueous medium such as, for example, dimethylformamide, tetrahydrofuran, acetonitrile or a halohydrocarbon such as dichloromethane at a temperature within the range $-25°$ C to $+150°$ C. The reaction may optionally be carried out in the presence of a base such as triethylamine or pyridine and the base may also be used as the solvent for reaction.

Where acid chlorides are used, the reaction may be carried out using the Schotten-Baumann technique in the presence of a suitable base, for example, aqueous sodium hydroxide, conveniently at a temperature between 0° C. and 100° C., for example, room temperature.

According to another general process (4a), the compounds of general formula (I) may be prepared by treating a compound of formula (VIIIa)

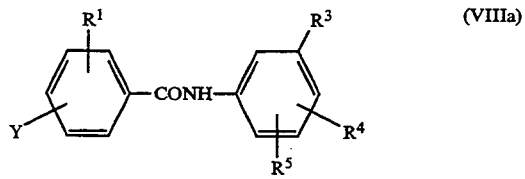

(VIIIa)

(where Y represents a bromine or iodine atom or the group $-OSO_2CF_3$) with a compound of formula (IXa)

$$R^2B(OH)_2 \quad (IXa)$$

or an ester or an anhydride thereof.

Alternatively, according to the general process (4b), the compounds of general formula (I) may be prepared by treating a compound of formula (VIIIb)

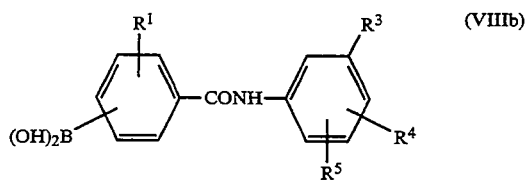

(VIIIb)

or an ester or an anhydride thereof, with a compound of formula (Ixb)

$$R^2-Y \quad (IXb)$$

where Y represents a bromine or iodine atom or the group $-OSO_2CF_3$.

Both reactions may be effected in the presence of a transition metal catalyst such as $(Ph_3P)_4Pd$ (where Ph represents phenyl) in a suitable solvent such as an ether (e.g. 1,2-dimethoxyethane or tetrahydrofuran) in the presence or absence of water, or an aromatic hydrocarbon (e.g. benzene). The reaction is preferably carried out in the presence of a base such as an alkali or alkaline earth metal carbonate (e.g. sodium carbonate) at a suitable temperature up to reflux.

Compounds of general formula (I) in which $R^2$, $R^4$ and $R^5$ have a particular meaning may be converted into another compound of the invention by standard methods of interconversion.

For instance, when $R^2$ contains a hydroxy or alkoxy group and/or when $R^4$ and/or $R^5$ represents hydroxy or alkoxy these groups may be interchanged by standard methods of O-alkylation or O-dealkylation. Thus, for example, a compound in which $R^4$ represents hydroxy may be prepared by treating a corresponding compound in which $R^4$ represents methoxy with a reagent system capable of removing the methyl group e.g. a mercaptide such as sodium ethylmercaptide in a solvent such as dimethylformamide, lithium iodide in collidine, boron tribromide in a halohydrocarbon solvent e.g. methylene chloride or molten pyridine hydrochloride.

When $R^2$ contains a hydroxymethyl group this may be converted by oxidation into a corresponding compound of general formula (I) in which $R^2$ contains a group $COR^6$ (where $R^6$ is a hydrogen atom) or $CO_2H$. Thus, for example, oxidation may be effected using a suitable oxidising agent such as a manganese oxidising agent (e.g. manganese dioxide) in a solvent such as an ether (e.g. 1,4-dioxan) at a suitable temperature up to reflux, a chromium oxidising agent (e.g. Jones reagent) or pyridinium dichromate in a suitable solvent such as a halohydrocarbon (e.g. methylene chloride).

When $R^2$ contains an aldehyde group this may be converted by oxidation into a corresponding compound of general formula (I) in which $R^2$ contains a group $CO_2H$. Thus, for example, oxidation may be effected using a suitable oxidising agent such as a source of silver (I) ions (e.g. silver nitrate) in aqueous alkali optionally in the presence of a cosolvent such as an alcohol (e.g. methanol).

Intermediates of formula (II) may be prepared from the corresponding compound of formula (X)

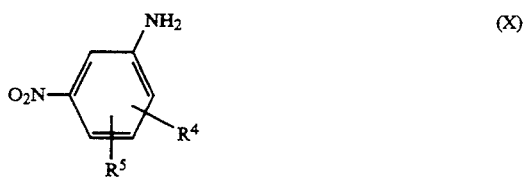

by reaction with a compound of formula (XI)

in the presence of acetic anhydride, followed by reduction of the diketopiperazine intermediate thus formed using, for example, borane. The reaction may be carried out at a temperature between 50° C. and reflux, and optionally in a solvent such as an ether, e.g. tetrahydrofuran, or toluene. The nitro group may be subsequently converted into an amine using standard methodology.

Alternatively, intermediates of formula (II) in which $R^4$ is adjacent to $R^3$, and $R^5$ is a hydrogen atom, may be prepared by nitration of a compound of formula (XII)

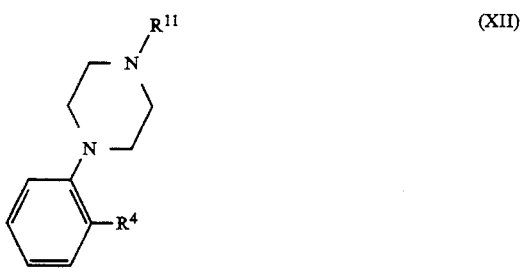

using an appropriate nitrating system such as sulphuric acid and potassium nitrate, or nitronium tetrafluoroborate, in the presence of a solvent, for example, acetonitrile, or alternatively, where $R^{11}$ is not a hydrogen atom, by nitrosation using, for example, sodium nitrite and a suitable acid such as sulphuric acid in solvent, for example, water, followed in each case by reduction of the nitro or nitroso group using standard methodology.

Intermediates of formula (IV) may be prepared by reduction of the corresponding nitro compound of general formula (XIII)

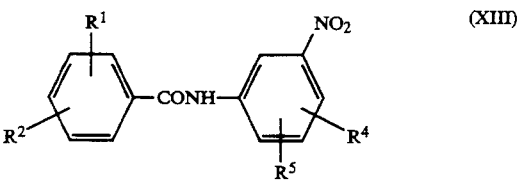

The reduction may be effected by catalytic hydrogenation using a metal catalyst such as palladium or platinum or oxides thereof, preferably, in a solvent such as an alcohol e.g. ethanol, or alternatively by using Raney nickel and hydrazine in a solvent such as an alcohol e.g. ethanol.

Intermediates of formula (XIII) may be prepared by condensing a compound of formula (VI) with a compound of formula (X) under the conditions of general process (3).

It will be appreciated that, where necessary, a halogen substituent may be converted into a carboxyl group using standard methodology thus, for example, intermediates of formula (VII) may be prepared from an intermediate of formula (III) by lithiation using, for example, n-butyl lithium followed by quenching with carbon dioxide.

Intermediates of formula (VIIIa) and (VIIIb) may be prepared by reaction of a compound of formula (II) with a compound of formula (XIVa) or (XIVb), respectively,

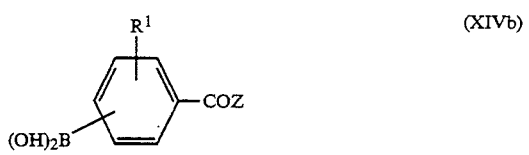

according to the method of general process (3).

The boronic acid intermediates of formulae (VIIIb), (IXa) and (XIVb) or their esters or anhydrides may be used in situ under the conditions described above for general process (4).

Intermediates of formula (VII) may be prepared by the reaction of a compound of formula (IXa) or (IXb) with a compound of formula (XIVa) or (XIVb), respectively, according to the method of general process (4).

Intermediates of formula (II) may also be prepared from the corresponding carboxylic acid using conventional procedures (e.g. by Curtius rearrangement).

Intermediates of formulae (V), (X), (XI), (XII), (XIVa) and (XIVb) are either known compounds or may be prepared by standard methodology or methods analogous to those described herein.

Physiologically acceptable acid addition salts of the compounds of general formula (I) may be prepared by treating the corresponding free base with a suitable acid using conventional methods. Thus, for example, a generally convenient method of forming the acid addition salts is to mix appropriate quantities of the free base and the acid in an appropriate solvent e.g. an alcohol such as ethanol or an ester such as ethyl acetate.

Inorganic basic salts of compounds of general formula (I) may be prepared by treating the corresponding acid of general formula (I) (i.e. a compound of general formula (I) in which $R^2$ contains a group $CO_2H$) with a suitable base using conventional methods.

Salts of compounds of general formula (I) may also be converted into different physiologically acceptable salts of compounds of general formula (I) using conventional methods.

The invention is illustrated but not limited by the following examples in which temperatures are in °C. Thin layer chromatography (t.l.c.) was carried out on silica plates. 'Dried' refers to drying using sodium sulphate or magnesium sulphate unless otherwise stated. Flash column chromatography (FCC) was carried out on silica gel (Merck 9385) unless otherwise stated. Short path column chromatography (SPC) was carried out on silica gel (Merck 7747) unless otherwise stated.

The following solvent systems were used: System A—dichloromethane:ethanol:0.88 ammonia; System B—dichloromethane:methanol:0.88 ammonia.

The following abbreviations are used: ether—diethyl ether; DMF—1,2-dimethylformamide; THF—tetrahydrofuran; AIBN—azoisobutyronitrile; DME—1,2-dimethoxyethane.

Intermediate 1

[4-(Methylsulphinyl)phenyl]boronic acid

A solution of [4-(methylthio)phenyl]boronic acid (1.008 g) in acetonitrile (60 ml) and water (6 ml) was cooled with a dry ice-acetone bath until it just began to freeze. A solution of ceric ammonium nitrate (6.72 g) in water (10 ml) was added with swirling. The resulting solution was left to warm to room temperature. The mixture was then basified to pH5 by addition of 8% aqueous sodium bicarbonate (16 ml) and evaporated to dryness by re-evaporation with absolute ethanol. The dried residue was purified by SPC (Merck 7729) using ethyl acetate-ethanol (9:1 followed by 4:1 and 7:3) as eluent, to give a colourless solid. The solid was further purified by FCC eluting with dichloromethane:ethanol (9:1) to give the title compound (1.00 g) as a colourless gum.

T.l.c. Dichloromethane:ethanol (9:1) Rf 0.35.

The gum was dissolved in warm water and the solution evaporated to give a colourless crystalline solid (847 mg). Recrystallisation from water (15 ml) gave the title compound (697 mg) as almost colourless needles.

Analysis Found: C,45.6; H,4.85; S,17.55. $C_7H_9BO_3S$ requires: C,45.7; H,4.95; S,17.4%

Intermediate 2

[4-[[(1,1-Dimethylethyl)dimethylsilyl]oxy]phenyl]boronic acid, bimolecular anhydride n-Butyl lithium (1.6M; 9.7 ml) was added, over 8 min, under nitrogen to a stirred, cooled (−70°) solution of 1-bromo-4-[[(1,1-dimethylethyl)dimethylsilyl]oxy]benzene (4 g) in dry THF (40 ml). After a further 25 min, the resulting solution was added over 10 min to a stirred cooled (−66°) solution of tri-isopropyl borate (10 ml) in THF (40 ml) and the mixture stirred at room temperature for 2 h. Water (10 ml) and, after a further 5 min, pH 6.5 phosphate buffer (100 ml) and ether (50 ml) were added and the mixture stirred vigorously for 10 min. The aqueous layer was extracted with ether (2×70 ml) and the combined organic solutions dried and evaporated in vacuo to leave a white solid. Crystallisation from ether gave the title compound (2.02 g) as a white solid.

T.l.c. dichloromethane-methanol (96:4) Rf 0.56

Intermediate 3

4-Bromo-3-methylbenzenemethanol

Diborane in THF (1M; 220 ml) was added dropwise to a solution of 4-bromo-3-methylbenzoic acid (20.0 g) in THF (100 ml) at room temperature under nitrogen. The solution was stirred for 5 h, treated cautiously with water (20 ml) and aqueous sodium hydroxide (2N; 200 ml) and extracted with ether (3×100 ml). The dried extract was evaporated to give the title compound as a colourless oil (11.8 g).

T.l.c. hexane:ether (1:1) Rf. 0.35.

Intermediate 4

(4-Acetylphenyl)boronic acid n-Butyllithium (81.6 ml) was added dropwise to a stirred solution of 2-(4-bromophenyl)-2-methyl-1,3-dioxolane (30.0 g) in dry THF (400 ml), under nitrogen, at −75° C. After a period of 1.5 h, triisopropylborate (31.2 ml) was added dropwise at −75° C. The reaction was allowed to warm to room temperature over a 3 h period. Hydrochloric acid (2N; 200 ml) was added and the reaction was allowed to stand at room temperature overnight. The solvent was evaporated and the residue was purified by FCC eluting with ether to give a white solid which was purified by crystallisation from water (200 ml) to give the title compound (14.52 g) as a white crystalline solid m.p. 268°–270° C.

Intermediate 5

Methyl 4-methoxy-3-(4-methyl-1-piperazinyl)benzoate hydrochloride

A suspension of 2-chloro-N-(2-chloroethyl)-N-methylethanamine hydrochloride (1.92 g) and methyl 3-amino-4-methoxybenzoate (1.81 g) in n-butanol was refluxed with stirring for 19 h. Anhydrous sodium carbonate (0.54 g) was added and refluxing continued for 8.5 h. The solvent was then removed to give an oil which was taken up in water (50 ml) and 2N hydrochloric acid (50 ml) and extracted with ethyl acetate (2×50 ml). The acid solution was then basified with sodium bicarbonate and re-extracted with ethyl acetate (3×50 ml). The extracts were dried and concentrated to a semi-solid (2.47 g) which was absorbed from System A (200:8:1) (5 ml) onto Kieselgel G (100 g). Elution with the same solvent gave starting material and minor basic impurities. Further elution with System A (100:8:1) (450 ml) gave first minor impurities and later fractions afforded the free base of the desired product as a gum (0.48 g). This was taken up in methanol (5 ml), filtered and treated with ethereal hydrogen chloride and diluted to 25 ml with ethyl acetate. A cream coloured solid separated and was collected giving the title compound (0.586 g), m.p. 190°–194°. Recrystallisation from methanol-ethyl acetate afforded a sample for analysis.

Analysis Found: C,55.7; H,7.2; N,9.2; Cl,12.0 $C_{14}H_{20}N_2O_3 \cdot HCl$ requires C,55.9; H,7.0; N,9.3; Cl,11.8%

Intermediate 6

4-Methoxy-3-(4-methyl-1-piperazinyl)benzoic acid hydrazide

A solution of the free base of Intermediate 5 (2 g) in methanol (20 ml) was treated with hydrazine hydrate (4 ml) and refluxed under nitrogen for 16 h. The solution was evaporated and then adsorbed from ethanol onto silica gel [Merck Art. 7734, 5 g]. The product was purified from a plug of this silica gel by SPC eluting with System A (91:9:0.9) to give title compound as an off white solid (0.764 g).

T.l.c. System A (90:10:0.1), Rf 0.2

Intermediate 7

4-Methoxy-3-(4-methyl-1-piperazinyl)benzenamine

A solution of Intermediate 6 (0.73 g) in water (30 ml) was mixed with concentrated hydrochloric acid (0.6 ml), the solution cooled to 0°–5° C. and a solution of sodium nitrite (0.219 g) in water (10 ml) added during 5 min. The solution was stirred at 0°–5° C. for 20 min, then 1 h at 23° C., and treated with concentrated hydrochloric acid (40 ml) and acetic acid (40 ml). The mixture was heated at reflux for 2 h, cooled and poured into aqueous sodium hydroxide (5N; 260 ml). The mixture was extracted with ethyl acetate (3×500 ml), and the combined, dried organic extracts were evaporated to give the title compound (0.190 g), as gum.

T.l.c. System A (95:5:0.5), Rf 0.2

Intermediate 7 was also made by the alternative two-step reaction as follows:

(a) 1-Methyl-4-(2-methoxy-5-nitrophenyl)piperazine 1-(2-Methoxyphenyl)-4-methylpiperazine (5.36 g) was acidified with 5N sulphuric acid and the excess water evaporated in vacuo. Concentrated sulphuric acid (95–98%, 22 ml) was added and the mixture stirred at room temperature until homogeneous. To the stirred, dark solution was added portionwise at room temperature potassium nitrate (3.07 g) in ten portions at intervals of approximately 5 min. The mixture was stirred at room temperature for 4 h then poured onto ice (~500 ml) and the mixture made slightly alkaline with anhydrous sodium carbonate. The basic mixture was extracted with ethyl acetate (4×150 ml) and the combined extracts dried. After 1 h the mixture was filtered and the filtrate evaporated to dryness in vacuo. The dark red residue was diluted with ether (200 ml) and the solid which separated (0.51 g) was filtered off and discarded. The filtrate was evaporated to dryness and the oily residue mixed with ether (300 ml) and the suspension filtered. The filtrate was evaporated to dryness to give a red gum which very slowly solidified to give the title compound (5.45 g)

T.l.c System A (150:8:1), Rf 0.45

(b) 4-Methoxy-3-(4-methyl-1-piperazinyl)benzeneamine

To a solution of the product of step (a) (5.07 g) in ethanol (70 ml) was added a paste of Raney Nickel in water (2 g). To the warmed suspension was added, with constant agitation, hydrazine hydrate (5 ml) dropwise during 20 min with occasional warming. After the main effervescence had ceased, the suspension was heated for 15 min and then filtered with the aid of ethanol under nitrogen. The residues were kept moist and washed with ethanol and the combined filtrate and washings were evaporated to dryness with the aid of ethanol. The dark residue was re-evaporated with ethanol (20 ml), resuspended in ether (40 ml) and the mixture filtered. The residue was washed with ether and dried to give a solid consisting of the title compound (2.365 g)

T.l.c System A (70:8:1), Rf 0.25.

A further yield of the title compound (0.58 g) was recovered from the ether filtrates and had t.l.c. (as above) Rf 0.25.

Intermediate 8

4-Bromo-N-[4-methoxy-3-(4-methyl-1-piperazinyl)-phenyl]benzamide

A solution of Intermediate 7 (0.168 g) in pyridine (3 ml) was treated with 4-bromobenzoyl chloride (0.25 g) and stirred at 110°, under nitrogen, for 5 h. Sodium bicarbonate (20 ml; 8%) was added and the mixture was evaporated. The product was pre-adsorbed onto silica gel [Merck Art. 7734 ca. 5 g] and purified by SPC eluting with System A (97:3:0.3) to give the title compound as a beige solid (0.237 g), m.p. 158.5°–159.5° C.

Intermediate 9

4-Bromo-N-[4-methoxy-3-(4-methyl-1-piperazinyl)-phenyl]-3-methylbenzamide

4-Bromo-3-methylbenzoic acid (4.86 g) in an excess of thionyl chloride (25 ml) was heated to reflux for ca. 1 h. The excess thionyl chloride was then removed by distillation and evaporation. The acid chloride was then added to a mixture of a solution of Intermediate 7 (5.0 g) in THF (25 ml) and sodium hydroxide (1.8 g) in water (30 ml). The resulting solution was then stirred at room temperature, under nitrogen, overnight. The solvent was removed by evaporation, water (40 ml) added and the mixture extracted with dichloromethane (5×50 ml), dried and evaporated to give a brown/orange sticky foam. This was purified by FCC eluting with System B (970:20:10) to give the title compound (5.73 g).

T.l.c. System B (970:20:10) Rf=0.11

Intermediate 10

[4-[[[4-Methoxy-3-(4-methyl-1-piperazinyl)phenyl]amino]carbonyl]-2-methylphenyl]boronic acid Butyl lithium (21.5 ml of a 1.6M solution in hexane) was added dropwise to a stirred solution of Intermediate 9 (5.77 g) in dry THF (60 ml) at −78° C. under nitrogen. After leaving at −78° C. for 1 h the mixture was warmed to 0° C. and then cooled down again to −78° C. Triisopropylborate (7.96 ml, 6.48 g) was added dropwise and the mixture stirred at −78° C. for 30 min before warming to room temperature for a further hour. Water (20 ml) was added and hydrochloric acid (2N) added to pH7. The volume of the mixture was reduced by evaporation, silica (Merck 9385) added and the mixture evaporated to dryness. This was then applied to a column of silica and purified by column chromatography eluting with System B (945:50:5) to give firstly recovered starting material followed by the title compound as a pale yellow foam (1.87 g) m.p. 78°–80° C.

T.l.c. System B (890:100:10) Rf=0.07.

Similarly prepared was:

Intermediate 11

[4-[[[4-Methoxy-3-(4-methyl-1-piperazinyl)phenyl]amino]carbonyl]phenyl]boronic acid as a cream-coloured foam (280 mg).

T.l.c. System A (50:45:5) Rf 0.04

From n-Butyllithium (7.5 ml of 1.6M solution in hexane), added dropwise at −90° to −100° to a stirred solution of Intermediate 8 (404 mg) and triisopropylborate (2.77 ml) in dry THF (20 ml).

Intermediate 12

4-Bromo-3-methylbenzenemethanamine

Borane in THF (25.5 ml) was added dropwise, at 0° C., under nitrogen to a solution of 4-bromo-3-methylbenzonitrile (1.0 g) in THF (dry, 20 ml). The solution was left at 0° C. for 30 min and then stirred at room temperature overnight. Methanol was added carefully to quench the reaction. Hydrochloric acid (2N, 20 ml) was added and the solution stirred at room temperature for 4 h. Further 2N hydrochloric acid (20 ml) was added and the mixture heated to reflux for several hours. Sodium bicarbonate was added to the cooled mixture till basic and extracted with dichloromethane (4×50 ml), dried and slowly evaporated to give an orange/yellow oil. This was then applied in methanol to a flash column of silica gel which was eluted with hexane: ethyl acetate (1:1)→ethyl acetate:methanol:0.88 ammonia (790:200:10) to give the title compound as a yellow/orange oil (364 mg).

T.l.c. ethyl acetate:methanol:ammonia (890:100:10) Rf=0.42

Intermediate 13

Ethyl[(4-bromo-3-methylphenyl)methyl]carbamate

Ethyl chloroformate (0.73 ml, 0.82 g) was added dropwise to a stirring solution of Intermediate 12 (383 mg) in sodium hydroxide (0.5 g) in methanol (20 ml) under nitrogen at room temperature. The clear yellowish solution went white and cloudy and was stirred overnight. The mixture was evaporated to dryness and the resulting solid triturated with ether (ca. 30 ml). The solid was filtered off under vacuum, and the filtrate evaporated to dryness giving a yellow oil (446 mg). This was applied in the minimum volume of dichloromethane to a flash column of silica gel which was eluted with hexane:ethyl acetate (850:150) to give the title compound (314 mg) as a white solid, m.p. 180°–182° C.

Intermediate 14

4-Bromo-3,N-dimethylbenzamide

4-Bromo-3-methylbenzoic acid (20 g) was added to a suspension of 1,1-carbonyldiimidazole (18.1 g) in dry THF (250 ml) at 5° C. and the resulting suspension stirred for 2.5 h at 5° C. Methylamine (33% w/v, solution in methanol 50 ml) was added dropwise over 5 min and the resultant mixture stirred at 23° for 15 h. The solution was evaporated and the residue treated with aqueous 2M-hydrochloric acid (150 ml). The mixture was extracted with ether (4×150 ml) and the combined, dried organic extracts were evaporated. The residue crystallised from hot ethyl acetate (~50 ml) to give the title compound as white crystals (8.7 g), Analysis Found: C,47.3; H,4.4; N,6.1;Br, 34.9 $C_9H_{10}BrNO$ requires C,47.4; H,4.4; N,6.1; Br, 35.0%

Intermediate 15

4-Bromo-3,N-dimethylbenzenemethanamine

Borane (1.0M solution in THF, 187 ml) was added to a stirred solution of Intermediate 14 (8.54 g) in dry THF (50 ml) under nitrogen at 23° C. over 15 min. After 2.5 h, the solution was stirred at reflux for 3.5 h, cooled, and aqueous 5M sodium hydroxide was added cautiously over 15 min (220 ml). The aqueous layer was separated, extracted with ether (4×250 ml), and the combined, dried organic layers were evaporated. The residual oil was purified by vacuum distillation to give the title compound as a colourless oil (3.8 g).

T.l.c. System A (89:10:1) Rf=0.34.

Intermediate 16

N-[(4-Bromo-3-methylphenyl)methyl]-2-methoxy-N-methylacetamide

Methoxyacetylchloride (0.96 ml) was added dropwise at 0°–5° to a stirred solution of Intermediate 15 (1.50 g) in dry pyridine (10 ml) and stirring continued at 0°–5° for 1 h. The mixture was stirred at 23° for 15 h, treated with aqueous saturated sodium bicarbonate (10 ml), and evaporated. The mixture was evaporated, treated with water (30 ml), and extracted with ethyl acetate (3×30 ml). The combined, dried organic extracts were evaporated and the residual oil purified by FCC eluting with a gradient of ethyl acetate-hexane (1:1→4:1) to give the title compound as a pale yellow oil (779 mg).

T.l.c. ethyl acetate:hexane (1:1) Rf=0.17

Intermediate 17

1-Bromo-4-(chloromethyl)-2-methylbenzene

A solution of triphenylphosphine (7.83 g) in dichloromethane (25 ml) was added at −5° to 0° over 20 min to a stirred mixture of Intermediate 3 (4.00 g) in dichloromethane (100 ml) under nitrogen and the mixture stirred at room temperature for 37 days. The mixture was evaporated, treated with water (200 ml) and extracted with ether (2×250 ml). The combined dried organic extracts were evaporated and the residual oil purified by FCC eluting with hexane to give the title compound as a colourless oil (2.73 g).

T.l.c. (hexane) Rf 0.34.

Intermediate 18

1-Bromo-4-[(2-methoxyethoxy)methyl]-2-methylbenzene

Sodium hydride (368 mg of a 60% dispersion in oil) was washed under nitrogen with hexane (3×5 ml) and then treated with a solution of Intermediate 17 (1.80 g) in DMF (10 ml). 2-Methoxyethanol (0.65 ml) was added with stirring and cooling to maintain a temperature of 20°–25°. After 24 h, the mixture was evaporated, treated with water (20 ml), and extracted with ether (2×100 ml). The combined, dried organic extracts were evaporated, and the residue purified by FCC with ethyl acetate:hexane (10:90→15:85) to give the title compound as a colourless oil (1.76 g).

Analysis Found: C,51.2; H,6.0; Br, 31.0 $C_{11}H_{15}BrO_2$ requires: C,51.0; H,5.8; Br, 30.8%

Intermediate 19

4-Bromo-N,N,3-trimethylbenzamide

A mixture of 4-bromo-3-methylbenzoic acid (1.0 g) and thionyl chloride (3 ml) was refluxed under nitrogen for 1 h and evaporated. The residue in THF (10 ml) was treated with aqueous dimethylamine (40%; 3 ml) in one portion. The solution was left to cool to room temperature (15 min) and was treated with aqueous sodium carbonate (1M; 50 ml) and extracted with ethyl acetate (2×100 ml). The dried extract was evaporated to give the title compound as a colourless oil (0.95 g).

Tlc ether Rf 0.4

Intermediate 20

4-Bromo-N-methylbenzenesulphonamide

A solution of 4-bromobenzenesulphonyl chloride (2.0 g) in THF (5 ml) was treated in two portions with aqueous methylamine (40%; 6 ml). The resulting exothermic reaction was allowed to subside and the solution was diluted with water (10 ml) and extracted with dichloromethane (2×50 ml). The dried extract was evaporated to give the title compound as a white solid (2.0 g).

Tlc ether Rf 0.9.

Intermediate 21

N-(4-Bromo-3-methylphenyl)methanesulphonamide

Methanesulphonyl chloride (0.88 ml) was added dropwise to a stirred solution of 4-bromo-3-methylbenzenamine (1.02 g) in pyridine (9 ml) under nitrogen at −10° to −14° C. After 2 h, aqueous (8%) sodium bicarbonate (35.6 ml) was added and the mixture extracted with ethyl acetate (3×100 ml). The combined, dried organic extracts were evaporated and the residue crystallized from ethyl acetate to give the title compound as a white powder (100 mg). The mother liquors were evaporated onto silica gel (Merck 7734, 3 ml) and the residue applied as a plug to a flash column of silica gel (Merck 9385). Elution with hexane:ethyl acetate (85:15)

afforded a further sample of the title compound as a white solid (250 mg).

Assay Found: C,36.4; H,3.6; N,5.0%
$C_8H_{10}BrNO_2S.0.04H_2O$ requires C,36.3; H,3.8; N,5.3%
Water Assay: Found: $H_2O$ 0.32% w/w=0.04 mol

Intermediate 22

4-(4-Bromophenylmethyl)morpholine

A solution of 1-bromo-4-(bromomethyl)benzene (100 mg) in dry THF (10 ml) containing potassium carbonate (380 mg) was treated slowly with morpholine (0.32 ml, 317 mg). The resulting mixture was stirred at room temperature under nitrogen for 18 h, before filtering and concentrating in vacuo to give the title compound as a white solid (620 mg). m.p. 82°–83° C.

Intermediate 23

4-(4-Bromophenylmethyl)thiomorpholine

A solution of 1-bromo-4-(bromomethyl)benzene (760 mg) in dry THF (10 ml) containing potassium carbonate (386 mg) was treated dropwise with thiomorpholine (0.36 ml, 369 mg). The resulting mixture was stirred at room temperature under nitrogen for 20 h before filtering and concentrating in vacuo to give impure title compound which was purified by FCC eluting with dichloromethane to give the title compound as a crystalline white solid (634 mg). m.p. 74°–75° C.

Intermediate 24

3-(4-Bromo-3-methylphenyl)-1,2,4-oxadiazole

A solution of sodium methoxide (1.93 g) in methanol (15 ml) was added dropwise over 10 min to a solution of hydroxylamine hydrochloride (2.48 g) in methanol (30 ml). The mixture was stirred for 1 h at 20° and was then filtered. 4-Bromo-3-methylbenzonitrile (7 g) was then added to the filtrate, and the mixture was heated to reflux for 18 h. The solvent was then evaporated giving a grey solid, a portion of which (2.2 g) was dissolved in trimethoxymethane (20 ml) and was heated to reflux for 18 h. The cooled mixture was poured into water (100 ml) and extracted with ethyl acetate (2×100 ml). Evaporation of the dried extracts gave a pale green oil (1.8 g). This material was chromatographed on silica gel (Merck 9385) eluting with ethyl acetate:hexane (1:5) to give the title compound as a colourless solid (656 mg).

T.l.c. ethyl acetate:hexane (1:4) Rf 0.54.

Intermediate 25

4-Bromo-N,N,3-trimethylbenzenamine

Formaldehyde (37% aq: 2 ml) was added dropwise to a solution of 4-bromo-3-methylbenzenamine (1.0 g) in formic acid (2 ml). The solution was heated at 100° for 4 h, cooled and added to aqueous sodium bicarbonate (1N; 50 ml) and the dried extract was evaporated. The residue was purified on a column of silica (Merck 9385) eluted with hexane-ether (3:1) to give the title compound as a pale yellow solid (150 mg) m.p. 47°–49°.

Intermediate 26

3-Chloro-4-hydroxy-N,N-dimethylbenzamide

A suspension of 3-chloro-4-hydroxybenzoic acid hemihydrate (3.0 g) in thionyl chloride (10 ml) was refluxed under nitrogen for 2 h. Tetrahydrofuran (10 ml) was added to aid solubility and the suspension was refluxed for 3 h and evaporated. The residue was suspended in THF (20 ml) and was treated in 3 portions with aqueous dimethylamine (40%; 15 ml). The solution was stirred for 1 h, treated with aqueous sodium bicarbonate (1N; 50 ml) and extracted with dichloromethane-methanol ( 19:1; 3×100 ml). The dried extract was evaporated and the residue was crystallized from ethyl acetate (30 ml) to give the title compound as a white solid (1.0 g).

T.l.c. ether Rf 0.3.

Intermediate 27

2-Chloro-4-[(dimethylamino)carbonyl]Phenyltrifluoromethanesulphonate

Trifluoromethanesulphonic anhydride (315 mg) was added dropwise to a solution of Intermediate 26 (250 mg) and pyridine (0.2 ml) in dichloromethane (5 ml) at 0° C. under nitrogen. The solution was stirred at room temperature for 1 h and added to hydrochloric acid (1N;25 ml). The mixture was extracted with dichloromethane (25 ml) and the dried extract was evaporated. The residue was purified on a column of silica (Merck 9385) eluted with ether to give the title compound as a colourless oil (333 mg).

T.l.c. ether Rf. 0.5.

Intermediate 28

4-Bromo-N-(2-methoxyethyl)-3-methylbenzamide

A solution of 4-bromo-3-methylbenzoic acid (3.65 g) in thionyl chloride (24 ml) under nitrogen was stirred at reflux for 20 min and evaporated. A solution of the residue in THF (20 ml) was treated with 2-methoxyethanamine (1.3 g) and stirred for 24 h under nitrogen. The solution was evaporated, the residue treated with sodium bicarbonate (50 ml) and extracted with ethyl acetate (6×50 ml). The combined, dried organic extracts were evaporated. The residue was absorbed from hot ethanol (20 ml) onto silica gel (Merck 7734) and this applied as a plug to a flash column of silica gel (Merck 9385). Gradient elution with hexane:ethyl acetate (3:1 to 1:1) gave the title compound (2.0 g) as a white solid. m.p. 79°–81° C.

Intermediate 29

4-Bromo-N-(2-methoxyethyl)-3,N-dimethylbenzamide

A solution of Intermediate 28 (1.5 g) in DMF (20 ml) was added to a stirred suspension of sodium hydride (0.32 g of a 60% dispersion in oil washed with cyclohexane (3×10 ml)) in dry DMF (5 ml) under nitrogen at 23° C. Iodomethane (0.74 ml) was added and the reaction stirred for 4 h. The reaction was then added via a syringe to 2M hydrochloric acid (16 ml) and water (10 ml). The mixture was evaporated, treated with water (70 ml), and extracted with ethyl acetate (3×100 ml). The combined organic extracts were evaporated and the residue purified by FCC eluting with ethyl acetate:hexane (1:1) to give the title compound (1.5 g) as a yellow oil.

T.l.c. hexane:ethyl acetate (1:1) Rf 0.3

Intermediate 30

4-(4-Bromo-3-methylbenzoyl)morpholine

A solution of 4-bromo-3-methylbenzoic acid (5.00 g) in dry THF (60 ml) was added dropwise at −5° to +5° to 1,1'-carbonylbis[1H-imidazole](4.90 g) and stirred under nitrogen over 10 min. Stirring was continued at +23° for 4 h, and morpholine (6.1 ml) added dropwise over 1 min. After 16 h the solution was evaporated, treated with aqueous 2M hydrochloric acid (80 ml), and extracted with ethyl acetate (4×75 ml). The combined, dried organic extracts were washed with aqueous saturated sodium bicarbonate (100 ml), dried and evaporated. A solution of the residual oil in dichloromethane (60 ml) was adsorbed onto silica gel (Merck 7734) and the mixture applied as a plug to a flash column of silica gel (Merck 9385). Gradient elution with ethyl acetate:-hexane (3:7→6:4) afforded the title compound as a cream solid (5.75 g).

Analysis Found: C,50.8; H,5.0; N,4.9; Br,28.3. $C_{12}H_{14}BrNO_2$ requires C,50.7; H,5.0; N,4.9; Br,28.1%

Intermediate 31

Methyl-4-bromo-3-methylbenzoate

4-Bromo-3-methylbenzoic acid (10 g) was suspended in methanol (50 ml) containing conc. sulphuric acid (2 ml). The mixture was heated to reflux for 18 h. On addition of 8% NaHCO$_3$ (100 ml) to the cooled reaction, a flocculent solid was filtered off and dried in vacuo at 40°–45° to give the title compound as a liquid which recrystallised on cooling (10.25 g) m.p. 39.5°–40.5°.

Intermediate 32

4-(Trifluoromethyl)phenyl trifluoromethanesulphonate

A solution of trifluoromethanesulphonic anhydride (1.0 g) in dichloromethane (2 ml) was added dropwise to a solution of 4-(trifluoromethyl)phenol (0.5 g) in dichloromethane (10 ml) and pyridine (0.5 ml) at 0° under nitrogen. The resulting suspension was stirred for 1 h at room temperature, diluted with dichloromethane (20 ml) and washed with aqueous sodium carbonate (2N; 20 ml). The dried organic phase was evaporated and the residue was purified by FCC eluting with ether to give the title compound as a colourless oil (710 mg).

T.l.c. ether Rf 0.8.

Intermediate 33

4-bromo-N,N,3-trimethylbenzamide

A mixture of 4-bromo-3-methylbenzoic acid (1.0 g) and thionyl chloride (3 ml) was refluxed under nitrogen for 1 h and evaporated. The residue in THF (10 ml) was treated with aqueous dimethylamine (40% ; 3 ml) in one portion. The solution was left to cool to room temperature (15 min) and was treated with aqueous sodium carbonate (1M; 50 ml) and extracted with ethyl acetate (2×100 ml). The dried extract was evaporated to give the title compound as a colourless oil (0.95 g).

T.l.c. ether Rf 0.4.

Intermediate 34

1-(2-Chloro-5-nitrophenyl)-4-methylpiperazine

A mixture of 2-chloro-5-nitrobenzenamine (7.95 g) and 2-chloro-N-(2-chloroethyl)-N-methylethanamine hydrochloride (8.86 g) in chlorobenzene (40 ml) under nitrogen was heated to reflux for 3 days before cooling and diluting with dichloromethane (60 ml). The reaction mixture was then extracted with water (2×500 ml), the aqueous layers combined and basified with 2N sodium hydroxide, then extracted with dichloromethane (4×400 ml). The combined, dried extracts were concentrated in vacuo to give a dark brown oil (7.82 g) which was purified by flash column chromatography eluting with ether to give a dark brown oil which crystallised upon standing. The material was dissolved in ethanol (40 ml) and boiled up with some charcoal (300 mg). The hot ethanolic suspension was filtered and concentrated in vacuo to give the title compound as a yellow oil which crystallised on standing (5.25 g) m.p.63°–64° C.

Intermediate 35

4-Chloro-3-(4-methyl-1-piperazinyl)benzenamine

A solution of Intermediate 34 (5.06 g) in ethanol (60 ml) and water (10 ml) was treated with Raney Nickel (2 g of a slurry in water) under nitrogen. This mixture was cooled to 18° C. and treated dropwise with hydrazine hydrate (4 ml) over 15 minutes. The resultant mixture was stirred at room temperature for 2 hours before filtering. The filtrate was concentrated in vacuo to give an oil which crystallised upon cooling. The pale brown crystalline solid was dried in vacuo to give the title compound as a brown crystalline solid (4.36 g) m.p 96°–97° C.

Intermediate 36

[4-[[[4-Chloro-3-(4-methyl-1-piperazinyl)phenyl]amino]carbonyl]phenyl]boronic acid To a cooled (0°) stirred solution of (4-carboxyphenyl)boronic acid (166 mg) in dry pyridine (5 ml) was added thionyl chloride (0.08 ml). The mixture was stirred for 30 mins and then Intermediate 35 (225 mg) was added. Stirring was maintained at 20° for 18 h. Water (40 ml) was added and the mixture was washed with ethyl acetate (2×40 ml). The precipitate which formed in the aqueous layer was collected and dried to give the title compound (196 mg).

Tlc System A (10:8:1) Rf 0.1

Intermediate 37

1-(2-Fluoro-5-nitrophenyl)-4-methylpiperazine

A mixture of 2-fluoro-5-nitrobenzenamine (4.06 g) and 2-chloro-N-(2-chloroethyl)-N-methylethanamine hydrochloride (5.006 g) in chlorobenzene (20 ml) was heated at reflux under nitrogen for 2½ days. The dark solid was dissolved in methanol (150 ml) and the solution was then concentrated in vacuo onto silica and purified by FCC eluting with System A (400:8:1) to give impure material (1.9 g). This was purified again by FCC eluting with System A (300:8:1) to give the title compound as a crystalline brown solid (360 mg).

T.l.c. System A (400:8:1) Rf 0.15

Intermediate 38

4-Fluoro-3-(4-methyl-1-piperazinyl)benzenamine

A solution of Intermediate 37 (350 mg) in ethanol/water (5:2,10 ml) was added under vacuum to a prehydrogenated suspension of 10% palladium on carbon, 50% paste (166 mg) in ethanol/water (5:2, 4 ml). The resulting suspension was stirred at room temperature under an atmosphere of hydrogen for 30 minutes. The suspension was filtered through hyflo, and the filtercake washed with ethanol/water (5:2,50 ml). The combined filtrates were concentrated in vacuo, the residue dissolved in dichloromethane (20 ml) and dried. The filtered solution was concentrated in vacuo to give the title compound as a buff coloured solid (272 mg) m.p. 155°–156° C.

Intermediate 39

4-Bromo-3-methyl-N-[4-fluoro-3-(4-methyl-1-piperazinyl)phenyl] benzamide

A suspension of 4-bromo-3-methylbenzoic acid (3.01 g) in thionyl chloride (10 ml) was heated to reflux under nitrogen for 4 hours. After this time excess thionyl chloride was removed in vacuo, the residue diluted with THF and the solution added dropwise to a solution of Intermediate 38 (1.90 g) in THF (15 ml) containing water (5 ml) and sodium hydroxide (930 mg). The mixture was stirred at room temperature for 24 hours before removing excess THF in vacuo. The aqueous residue was diluted with water (20 ml) and extracted with dichloromethane (3×75 ml). The combined, dried extracts were concentrated in vacuo to give a dark brown oil which was purified by FCC eluting with System A (350:8:1 gradient to 200:8:1) to give an orange oil (4.29 g) which was dried in vacuo to give the title compound as a pale brown foam (3.436 g)

Analysis: Found: C,55.0 : H, 5.1 : N, 10.0 $C_{19}H_{21}BrFN_3O.0.3C_2H_5O.0.3H_2O$ Requires: C, 55.3; H, 5.5; N, 9.9%

Intermediate 40

[4-[[[4-Fluoro-3-(4-methyl-1-piperazinyl)phenyl]amino]carbonyl]-2-methylphenyl]boronic acid A solution of Intermediate 39 (2.917 g) in dry THF (30 ml) at −77° C., was treated dropwise with n-butyl lithium (15.5 ml of 1.64M solution in hexane) over 20 min, under nitrogen. The solution was stirred at −76° C. for 15 min before treating with triisopropyl borate (5.8 ml). The resulting mixture was allowed to warm to room temperature while stirring, over 2 hours, before treating with water (10 ml). Excess solvent was removed in vacuo, and the aqueous residue neutralised (to pH6) with 2N hydrochloric acid. The solution was left to cool, during which time an oily gum separated out. The aqueous layer was decanted and the oily gum triturated with ether (3×25 ml) to give the title compound as a cream-coloured powdery solid (2.063 g).

n.m.r. ($CH_3OD$) δ2.42 (3H,s), 2.59 (3H,s), 2.96 (4H,m), 3.23 (4H,m), 7.05 (1H,dd), 7.30 (1H,ddd), 7.40 (1H,br.d), 7.52 (1H,dd), 7.75–7.66 (1H,m).

Intermediate 41

1-[4-Methoxy-3-(trifluoromethyl)phenyl]ethanone

A solution 1-methoxy-2-(trifluoromethyl)benzene (3.52 g) was dissolved in glacial acetic acid (30 ml) and treated with boron trifluoride acetic acid complex (30 ml) and the resulting solution maintained at 55° for 48 hours. The solution was poured into dilute hydrochloric acid (100 ml) and ice (100 g) added and the mixture extracted with chloroform (2×200 ml). The combined organic extracts were washed with sodium bicarbonate solution (3×100 ml), then water (100 ml), dried and evaporated to dryness to give an oily black solid. This was chromatographed on silica (40 g) eluting with ether:light petroleum (bp.60°–80°) (1:4) to give a solid which was crystallised from light petroleum (bp.60°–80°) to give the title compound (0.3 g), m.p.56°–57°

Intermediate 42

1-[4-Hydroxy-3-(trifluoromethyl)phenyl]ethanone

A mixture of Intermediate 41 (800 mg) and pyridine hydrochloride (4 g) was heated to 180° under nitrogen and stirred overnight. The mixture was allowed to cool to room temperature before the gum was dissolved in a mixture of 2N Sodium carbonate (50 ml) and dichloromethane (50 ml). The organic layer was separated and the aqueous layer extracted further with dichloromethane (3×50 ml). The combined organic extracts were dried, concentrated in vacuo and the residue dissolved in dichloromethane (40 ml), then extracted with 2N sodium hydroxide (60 ml). The aqueous extract was then washed with dichloromethane (2×50 ml), neutralised with 2N hydrochloric acid and extracted with dichloromethane (3×75 ml). The combined, dried organic extracts were concentrated in vacuo to give a dark yellow gummy glass (60 mg). The 2N sodium carbonate layer from initial extraction was neutralised with 2N hydrochloric acid and extracted with dichloromethane (2×50 ml). The combined, dried extracts were concentrated in vacuo to give a pale yellow solid (106 mg). The neutralised sodium carbonate layer and the sodium hydroxide layer were acidified with 2N hydrochloric acid. Both acidified layers were then extracted with dichloromethane (3×50 ml), and the combined, dried extracts were concentrated in vacuo to give the title compound as a pale yellow solid (274 mg). Further purification by FCC eluting with hexane:ethyl acetate (4:1) gave the title compound as a white crystalline solid (220 mg), m.p. 168°–170° C.

Intermediate 43

4-Acetyl-2-(trifluoromethyl)phenyl trifluoromethanesulphonate

A stirred solution of Intermediate 42 (200 mg) in dry dichloromethane (6 ml) containing dry pyridine (0.14 ml) was cooled to 0° C. under nitrogen and trifluoromethanesulphonic anhydride (0.25 ml) added slowly. The mixture was stirred at 0° C. for 1½ h before allowing to warm to room temperature. The reaction mixture was added to 8% sodium bicarbonate solution (25 ml) and was extracted with dichloromethane (3×15 ml). The combined, dried extracts were concentrated in vacuo to give a dark yellow oil which was purified by FCC eluting with hexane:ethyl acetate (12:1) and dried in vacuo to give an oil (298 mg). Further purification by FCC eluting with toluene:hexane (1:1) gave the title compound as a colourless oil (240 mg), Analysis Found: C,35.8; H,1.6; $C_{10}H_6O_4F_6S$ requires C,35.7; H,1.8%

Similarly prepared was

Intermediate 44

4-Acetyl-2-methoxyphenyl trifluoromethanesulphonate as a white crystalline solid (648 mg) m.p. 34°–34°.

From a solution of 1-(4-hydroxy-3-methoxyphenyl)ethanone (0.50 g) in dry dichloromethane (15 ml) containing dry pyridine (0.4 ml) and trifluoromethanesulphonic anhydride (0.8 ml).

Intermediate 45

4'-[(Dimethylamino)carbonyl]-2'-methyl-[1,1'-biphenyl]-4-carboxylic acid

A mixture of Intermediate 33 (3.75 g) and 4-boronobenzoic acid (2.334 g) in DME (75 ml) and sodium carbonate (2N, 25 ml) was treated under nitrogen with tetrakis(triphenylphosphine)palladium (0) (50 mg). The resulting mixture was heated to reflux and stirred for 20 hours before cooling to room temperature, adding to water (50 ml) and washing with dichloromethane (200 ml). Hydrochloric acid (2N) was added dropwise to the aqueous layer until pH 3 was obtained. The acidified aqueous layer was extracted with dichloromethane (3×200 ml) and the combined, dried extracts concentrated in vacuo to give the title compound as a pale yellow solid (4.58 g) m.p. 190°–192° C.

Intermediate 46

1-(2-Bromo-5-nitrophenyl)-4-methylpiperazine

A suspension of 2-bromo-5-nitrobenzenamine (26.0 g) and 2-chloro-N-(2-chloroethyl)-N-methylethanamine hydrochloride (23.0 g) in chlorobenzene (150 ml) was heated to reflux under nitrogen and stirred for 15 hours before cooling to room temperature. The gummy mixture was diluted with dichloromethane (150 ml) and extracted with water (4×400 ml, acidified with 2N HCl). The combined aqueous extracts were basified with 2N sodium hydroxide (to pH 12) and extracted with dichloromethane (4×500 ml). The combined organic extracts were dried and concentrated in vacuo to give a brown oil which was purified by FCC eluting with System A (300:8:1 gradient to 200:8:1) to give the title compound as a brown solid (9.498 g) m.p. 100°–103° C.

Intermediate 47

4-Bromo-3-(4-methyl-1-piperazinyl)benzenamine

A suspension of Intermediate 46 (8.68 g) in ethanol (80 ml) and water (20 ml), under nitrogen, was treated with Raney nickel (3 g of a slurry with water). The suspension was then cooled to 17° C. and maintained at a temperature below 28° C. during the slow addition of hydrazine hydrate (6 ml), over 20 min. The cooled mixture was then stirred under nitrogen for 2 hours and filtered through Hyflo. The filter cake was washed thoroughly with ethanol:water (280 ml, 6:1) and the combined filtrates were concentrated in vacuo to give a gummy solid which was dissolved in dichloromethane, dried and concentrated in vacuo to give a dark grey/brown solid. The solid was triturated in hexane:ether (1:1, 50 ml) overnight. The solid was filtered and dried to give the title compound as a solid (3.28 g). Further product was obtained by concentration of the filtrate in vacuo. The orange solid residue was purified by FCC eluting with System A (300:8:1) to give the title compound as a yellow solid (3.38 g). m.p. 120°–121.5° C.

Intermediate 48

1-(4-Bromo-3-methylbenzoyl)pyrrolidine

A mixture of 4-bromo-3-methylbenzoic acid (400 mg) and thionyl chloride (0.4 ml) was refluxed under nitrogen for 1 h and evaporated. The residue in THF (2 ml) was added to a solution of pyrrolidine (0.8 ml) in THF (2 ml). The suspension was stirred for 1 h, added to aqueous sodium carbonate (2N; 25 ml) and extracted with dichloromethane (2×25 ml). The dried extract was evaporated to give the title compound as a beige solid (430 mg) m.p. 55°–57°.

similarly prepared were:

Intermediate 49

4-Bromo-N-butyl-N,3-dimethylbenzamide as a yellow oil (485 mg).

T.l.c. ether Rf=0.85

From 4-bromo-3-methylbenzoic acid (400 mg), thionyl chloride (0.4 ml) and N-methyl-1-butanamine (0.8 ml).

Intermediate 50

4-Bromo-N-(1,1-dimethylethyl)-3-methylbenzamide as a white solid (430 mg) m.p. 124°–125° C.

From 4-bromo-3-methylbenzoic acid (400 mg), thionyl chloride (0.4 ml) and 1,1-dimethylethanamine (0.8 ml).

Intermediate 51

1-(4-Bromo-3-methylbenzoyl)azetidine as a white solid (445 mg) m.p. 104°–105° C.

From 4-bromo-3-methylbenzoic acid (400 mg), thionyl chloride (0.5 ml) and azetidine (1 g).

EXAMPLE 1

4'-Hydroxy-N-[4-methoxy-3-(4-methyl-1-piperazinyl)phenyl]-[1,1'-biphenyl]-4-carboxamide A catalytic quantity of tetrakis(triphenylphosphine)palladium (0) (0.021 g) was added to a degassed solution ($N_2$ bubbled through the solution for 5 min) of Intermediate 8 (0.145 g), Intermediate 2 (0.108 g) and sodium carbonate (0.114 g) in 1,2-dimethoxyethane (8 ml) and water (5 ml). The reaction mixture was then heated at reflux for 16 h, under nitrogen. The reaction contents were absorbed onto silica gel [Merck Art 7734] and the product purified from a plug of this silica by SPC eluting with System A (95:5:0.5) to give the title compound as a beige foam-like solid (0.098 g), m.p. 120°–123° C.

Analysis Found C,69.0; H,6.85; N,9.0. $C_{25}H_{27}N_3O_3 0.8$ $CH_3CO_2C_2H_5$ requires C.69.4; H,6.9; N,8.6%.

EXAMPLE 2

4'-(Hydroxymethyl)-N-[4-methoxy-3-(4-methyl-1-piperazinyl)phenyl]-2-methyl-[1,1'-biphenyl]-4-carboxamide 4-Bromobenzenemethanol (130 mg), Intermediate 10 (400 mg), tris(2-methylphenyl)phosphine (15 mg), palladium (II) acetate (10 mg), DMF (2 ml) and triethylamine (1 ml), were heated to reflux under nitrogen for 5 h. On cooling, water (20 ml) was added and the reaction mixture extracted with dichloromethane (3×40 ml), the extracts dried and evaporated to yield a green/orange oil (600 mg). This was purified by FCC eluting with System B (967:30:3) to give the title compound (49 mg) as a cream-coloured foam.

T.l.c. System B (967:30:3) Rf=0.03 n.m.r. (250 MHz, $CDCl_3$) δ2.34 (3H,s), 2.38 (3H, s), 2.65 (4H, br.m), 3.15 (4H, br.m), 3.88 (3H, s), 4.78 (2H, s), 6.85 (1H, m), 7.22–7.35 (5H, m), 7.45 (2H, ½AA'BB'), 7.7 (1H,dd), 7.78 (2H, m).

EXAMPLE 3

N-[4-Methoxy-3-(4-methyl-1-piperazinyl)phenyl]-2-methyl-4'-(methylsulphinyl)-[1,1'-biphenyl]-4-carboxamide A solution of sodium carbonate (147 mg) in water (5 ml) was added to a solution of Intermediate 9 (300 mg) in DME (10 ml) followed by tetrakis(triphenylphosphine)palladium (0) (32 mg) and Intermediate 1 (127 mg), and the stirred mixture heated at reflux under nitrogen for 9 h. A further quantity of Intermediate 1 (60 mg) was added and heating continued for 4 h. When cool, the mixture was evaporated, treated with water (30 ml) and extracted with ethyl acetate (6×50 ml). The combined, dried organic extracts were evaporated and the residue purified by FCC eluting with System A (89:10:1) to give a solid which crystallised from ethanol (5 ml) to give the title compound as fine white crystals (162 mg), m.p. 210°–212.5°.

Analysis Found: C,67.8; H,6.6; N,8.6; $C_{27}H_{31}N_3O_3S$ requires C,67.9; H,6.5; N,8.8%

Similarly prepared was:

EXAMPLE 4

4'-Acetyl-N-[4-methoxy-3-(4-methyl-1-piperazinyl)phenyl]-2-methyl-[1,1'-biphenyl]-4-carboxamide as fine white crystals (79 mg). m.p. 167°–169.5° C.

Analysis Found: C,71.1; H,7.0; N,8.7; $C_{28}H_{31}N_3O_3.0.78H_2O$ requires C,71.3; H,7.0; N,8.9% Water assay Found: $H_2O$, 2.97% w/w=0.78 mol From Intermediate 9 (400 mg) and two portions of Intermediate 4 (400 mg) and (100 mg).

EXAMPLE 5

N-[4-Methoxy-3-(4-methyl-1-piperazinyl)phenyl]-[1,1'-biphenyl]-4-carboxamide

A mixture of Intermediate 11 (100 mg), bromobenzene (47 mg), tetrakis (triphenylphosphine)palladium (0) (30 mg), DME (5 ml), and aqueous sodium carbonate (2N, 1 ml) was refluxed under nitrogen for 3 h. The mixture was treated with water (25 ml) and extracted with dichloromethane (3×20 ml). The dried extract was evaporated and the residue was purified on a column of silica eluting with System B (240:10:1) to give the title compound as a white foam (57 mg)

T.l.c. System B (90:10:1) Rf 0.6 Analysis Found: C,72.7; H,6.8; N,10.0 $C_{25}H_{27}N_3O_2.0.7H_2O$ requires C,72.5; H,6.7; N,10.1%

Similarly prepared was:

EXAMPLE 6

N-[4-Methoxy-3-(4-methyl-1-piperazinyl)phenyl]-2'-methyl-4'-methylamino-[1,1'-biphenyl]-4-carboxamide (165 mg)

T.l.c. System A (967:30:3) Rf=0.25 n.m.r. (250 MHz, DMSO d6) δ2.28 (6H, 2xs), 2.5 (4H, m), 2.76 (3H, d), 3.03 (4H, br.m), 3.82 (3H, s), 5.79 (1H, br.q), 6.5–6.58 (2H, m), 6.97 (1H, d), 7.06 (1h, d), 7.06 (1H, d), 7.35–7.6 (4H, m), 8.0 (2H, ½AA'BB'), 10.15 (1H, br.s).

From Intermediate 11 (1.3 g) and 4-bromo-3,N-dimethylbenzenamine (0.9 g).

EXAMPLE 7

Ethyl [4'-[[[4-methoxy-[3-(4-methyl-1-piperazinyl)]-phenyl]amino]carbonyl]-2-methyl-([1,1'-biphenyl]-4-yl)]methyl carbamate A stirred solution of Intermediate 13 (610 mg) in DMF (4 ml) containing triethylamine ( 2 ml), tris(2-methylphenyl)phosphine (40 mg) and palladium (II) acetate (20 mg), was treated with Intermediate 11 (0.950 g) in one portion. The mixture was heated to reflux under nitrogen for 5 h, water (20 ml) added and the cloudy mixture concentrated in vacuo to a volume of 10 ml, before extracting with dichloromethane:ethyl acetate (2:1, 50 ml). The organic extract was dried and concentrated in vacuo to give a dark orange oil (1.23 g) which was purified by FCC eluting with System A (160:8:1) to give the title compound as a pale brown friable solid (160 mg).

T.l.c System A (75:8:1) Rf=0.5 Analysis Found: C,68.4, H,7.1; N,10.25; $C_{30}H_{36}N_4O_4.0.5H_2O$ requires: C,68.6; H,7.1; N,10.7%

EXAMPLE 8

4'-[1-(Hydroxyimino)ethyl]-N-[4-methoxy-3-(4-methyl-1-piperazinyl) phenyl]-2-methyl-[1,1'-biphenyl]-4-carboxamide (Z)-2-butenedioate (1:1)

Hydroxylamine hydrochloride (532 mg) was added to a solution of the product of Example 4 (500 mg) in pyridine (9 ml) and the mixture stirred at 23° C. under nitrogen for 24 h. Aqueous saturated sodium bicarbonate (25 ml) was added and the mixture evaporated. Water (50 ml) was added and the mixture extracted with dichloromethane (6×80 ml). The combined dried organic extracts were evaporated, treated with (Z)-2-butenedioic acid (250 mg) followed by ethanol (50 ml) and heated to reflux. After 10 min, the mixture was filtered, and the filtrate stood at 23° for 16 h. The precipitate was collected to give the title compound-as a fine cream crystals (158 mg) m.p. 219°–223°.

Analysis Found C,64.7;H,6.2; N,9.3; $C_{28}H_{32}N_4O_3.C_4H_4O_4.0.16H_2O$ requires C,65.0;H,6,2; N,9.5% Water assay Found: H2O, 0.61% w/w≡0.16 mol

EXAMPLE 9

4'-[[[4-Methoxy-3-(4-methyl-1-piperazinyl)phenyl]amino]carbonyl]-2'-methyl-[1,1'-biphenyl]-4-dimethylcarbamate A mixture of 4-bromophenyl dimethylcarbamate (222 mg) and Intermediate 10 (350 mg) in DME (18 ml) was treated with a solution of sodium carbonate (194 mg) in water (9 ml) , followed by tetrakis(triphenylphosphine)-palladium (0) (42 mg) and the stirred mixture heated at reflux under nitrogen for 5 h. The mixture was evaporated, treated with water (30 ml), and extracted with ethyl acetate (6×40 ml). The combined dried organic extracts were evaporated and the residue purified by FCC eluting with a gradient of System A (967:30:43945:50:5) to give a dull white foam (355 mg). A portion of the foam (175 mg) was further purified by SPC (Merck 7729) eluting with a gradient of System A (967:30:3→956:40:4) to give the title compound as a white foam (175 mg) m.p. 90°–94° C.

T.l.c. System A (89:10:1) Rf 0.47

EXAMPLE 10

4'-[[(Methoxyacetyl)methylamino]methyl]-N-[4-methoxy-3-(4-methyl-1-piperazinyl)phenyl]-2'-methyl-[1,1'-biphenyl]-4-carboxamide hydrochloride A solution of sodium carbonate (144 mg) in water (5 ml), followed by tetrakis(triphenylphosphine)palladium (0) (31 mg) was added to a solution of Intermediate 11 (250 mg) and Intermediate 16 (194 mg) in DME (10 ml) and the stirred mixture heated at reflux under nitrogen for 4 h. The mixture was evaporated, treated with water (20 ml), and extracted with ethyl acetate (6×50 ml). The combined, dried organic extracts were evaporated, and the residue purified by FCC eluting with a gradient of System A (945:50:5→934:60:6) to give a light cream-coloured foam (159 mg). A portion of the foam (100 mg) in ethyl acetate (5 ml) was acidified to pH1 by the addition of ethereal hydrogen chloride and the precipitate filtered off to give the title compound as fine white crystals (50 mg).

Analysis Found: C,61.1; H,7.1; N,9.0; Cl, 7.1. $C_{31}H_{38}N_4O_4.1.2HCl.1.74H_2O$ requires C,61.3; H,7.1; N,9.2, Cl,7.1.% Water assay Found: H2O, 5.2% w/w≡1.74 mol H2O T.l.c. System A (89:10:1), Rf 0.48

EXAMPLE 11

4'-[(2-Methoxyethoxy)methyl]-N-[4-methoxy-3-(4-methyl-1-piperazinyl)phenyl]-2'-methyl-[1,1'-biphenyl]-4-carboxamide A solution of sodium carbonate (230 mg) in water (11 ml), followed by tetrakis(triphenylphosphine)palladium (0) (50 mg), was added to a mixture of Intermediate 18 (281 mg) and Intermediate 11 (400 mg) in DME (22 ml) and the stirred mixture heated at reflux under nitrogen for 6 h. The mixture was evaporated, treated with water (50 ml), and extracted with ethyl acetate (6×40 ml). The combined, dried organic extracts were evaporated, and the residual oil adsorbed from ethanol (30 ml) onto silica gel (Merck 7734). The resultant silica was applied as a plug to a flash column of silica gel which was eluted with a gradient of System A (967:30:3→956:40:4) to give the crude title compound (264 mg). This crystallised from ethyl acetate (6 ml) to give the title compound as fine white crystals (166 mg), m.p. 147°–148°.

Analysis Found: C,71.0; H,7.4; N,8.15; $C_{30}H_{37}N_3O_4.0.15H_2O$ requires C,71.2; H,7.4; N,8.3%
Water assay Found: $H_2O$, 0.54% w/w≡0.15 mol

EXAMPLE 12

N-[4-Methoxy-3-(4-methyl-1-piperazinyl)phenyl]-N,N',2,2'-tetramethyl-[1,1'-biphenyl]-4,4'-dicarboxamide A mixture of Intermediate 10 (250 mg), Intermediate 19 (160 mg), tetrakis(triphenylphosphine)palladium (0) (20 mg), DME (8 ml), and aqueous sodium carbonate (2N; 2 ml) was refluxed under nitrogen for 18 h. The mixture was added to water (50 ml) and extracted with dichloromethane (3×50 ml). The dried extract was evaporated and the residue was purified FCC eluting with System B (485:15:1.5) followed by (240:10:1) to give the title compound as a white foam (75 mg).

T.l.c. System B (240:10:1), Rf 0.3 n.m.r. (CDCl₃) δ2.06 (3H,s), 2.23 (3H,s), 2.37 (3H,s), 2.64 (4H, br.m), 3.14 (6H, br.s), 3.6 (4H, br.m), 3.88 (3H,s), 6.86 (1H,d), 7.11 (1H,d), 7.18 (1H,d), 7.23–7.32 (4H,m), 7.36 (1H, br.s), 7.71 (1H,dd), 7.77 (1H, br.s), 7.80 (1H, br.s).

Similarly prepared were:

EXAMPLE 13

N-[4-Methoxy-3-(4-methyl-1-piperazinyl)phenyl]-N',N',2-trimethyl-[1,1'-biphenyl]-4,4'-dicarboxamide as a white solid (175 mg) m.p. 177°–178° C.

T.l.c. System B (90:10:1) Rf 0.6.

From Intermediate 10 (250 mg) and 4-bromo-N,N-dimethylbenzamide (160 mg). Trituration with ether (2×1 ml) afforded the title compound.

EXAMPLE 14

N-[4-Methoxy-3-(4-methyl-1-piperazinyl)phenyl]-N',N',2'-trimethyl-[1,1'-biphenyl]-4,4'-dicarboxamide as a white foam (120 mg).

T.l.c. System B (240:10:1), Rf 0.15. Analysis Found: C,69.6; H,6.9; N,10.9; $C_{29}H_{34}N_4O_3.0.7H_2O$ requires C,69.8; H,7.15; N,11.2%

From Intermediate 11 (200 mg) and Intermediate 19 (145 mg).

EXAMPLE 15

4'-(Aminosulphonyl)-N-[4-methoxy-3-(4-methyl-1-piperazinyl)phenyl]-3-methyl-[1,1'-biphenyl]-4-carboxamide as a white solid (42 mg).

T.l.c. system B (90:10:1), Rf 0.45 n.m.r. (CH₃OD d₄) δ2.22 (3H,s), 2.28 (3H,s), 2.58 (4H,m), 3.04 (4H,m), 3.70 (3H,s), 7.45 (2H, ½AA'BB'), 7.72 (1H,dd), 7.8 (1H,br.s), 7.9 (2H, ½AA'BB').

From Intermediate 10 (250 mg) and 4-bromobenzenesulphonamide (165 mg). A second extraction with dichloromethane:methanol (9:1) (3×50 ml) gave a more pure sample which was triturated with ether (2×20 ml) to give the title compound.

EXAMPLE 16

N-[4-Methoxy-3-(4-methyl-1-piperazinyl)phenyl]-2-methyl-4'-[(methylamino)sulphonyl]-[1,1'-biphenyl]-4-carboxamide as a white solid (140 mg).

T.l.c. System B (90:10:1), Rf 0.5. Analysis Found: C,61.9; H,6.3; N,10.4; $C_{27}H_{32}N_4O_4S.0.8H_2O$ requires C,62.0; H,6.5; N,10.7%

From Intermediate 10 (250 mg) and Intermediate 20 (150 mg).

EXAMPLE 17

3'-Acetyl-N-[4-methoxy-3-(4-methyl-1-piperazinyl)phenyl]-3-methyl-[1,1'-biphenyl]-4-carboxamide as a pale yellow foam (221 mg) m.p. 82°–84° C.

T.l.c. System A (150:8:1), Rf=0.33

From Intermediate 10 (280 mg) and 3-bromoacetophenone (133 mg).

EXAMPLE 18

N-[4-Methoxy-3-(4-methyl-1-piperazinyl)phenol]-2-methyl-4'-(4-morpholinylmethyl)-[1,1'-biphenyl]-4-carboxamide as a pale yellow foam (95 mg) m.p. 80°–84° C.

n.m.r (CDCl₃) δ2.35 (3H, s), 2.37 (3H, s), 2.5 (4H, m), 2.64 (4H, m), 3.15 (4H, m), 3.57 (2H, s), 3.75 (4H,m), 3.88 (3H,s), 6.87 (1H, d), 7.24–7.43 (6H, m), 7.68–7.82 (3H, m).

From Intermediate 10 (250 mg) and Intermediate 22 (211 mg). Further purification by FCC eluting with System A (400:8:1) afforded the title compound as a pale yellow foam which was dried in vacuo at 60° C. for 30 h.

EXAMPLE 19

N-[4-Methoxy-3-(4-methyl-1-piperazinyl)phenyl]-3-methyl-4'-(4-thiomorpholinyl)-[1,1'-biphenyl]-4-carboxamide as a pale yellow foam (78 mg) m.p. 88°–90° C.

n.m.r. (CDCl₃) δ2.35 (3H,s), 2.37 (3H,s), 2.6–2.8 (12H,m), 3.15 (4H,m), 3.58 (2H,s), 3.88 (3H,s), 6.85 (1H,d), 7.25–7.4 (6H,m), 7.68–7.82 (3H,m).

From Intermediate 10 (254 mg) and Intermediate 23 (165 mg). Purification by FCC eluting with System A (150:8:1) afforded a viscous gum which was dissolved in ether and concentrated in vacuo to give a pale yellow foam. This was dried under high vacuum at 60° C. for 2 h to give the title compound.

EXAMPLE 20

N-[4-Methoxy-3-(4-methyl-1-piperazinyl)phenyl]-2'-methyl-4'-[(methylsulphonyl)amino]-[1,1'-biphenyl]-4-carboxamide Intermediate 21 (250 mg) was added to a solution of Intermediate 11 (470 mg), sodium carbonate (288 mg), and tetrakis(triphenylphosphine)palladium (0) (63 mg) in water (15 ml) and DME (30 ml) under nitrogen and the stirred mixture heated at reflux for 24 h. When cool, the mixture was evaporated onto silica gel (Merck 7734). The resultant silica was applied as a plug to a flash column of silica gel (Merck 9385) and elution with System A (967:30:3) gave a white foam (200 mg). This was further purified by recrystallization from ethyl acetate (5 ml) to give the title compound as fine cream crystals (20 mg) m.p. 220°–221° C.

n.m.r. (CDCl₃) δ2.28 (3H,s), 2.38 (3H, s), 2.63 (4H,m), 3.08 (3H,s), 3.16 (4H,m), 3.89 (3H,s), 6.86 (1H,d), 7.09–7.28 (2H,m), 7.2–7.35 (3H(+CHCl₃),m), 7.42 (2H, ½AA'BB'), 7.76 (1H,br.s), 7.93 (2H,½AA'BB')

EXAMPLE 21

N-[4-Methoxy-3-(4-methyl-1-piperazinyl)phenyl]-2-methyl-4'-(methylthio)-[1,1'-biphenyl]-4-carboxamide A mixture of 1-bromo-4-(methylthio)benzene (106 mg), Intermediate 10 (200 mg), sodium carbonate (111 mg), water (5 ml), and DME (10 ml) was stirred at reflux under nitrogen for 9 h. The cooled mixture was evaporated, shaken with water (30 ml) and ethyl acetate (40 ml), and filtered to give solid I. The aqueous phase was further extracted with ethyl acetate (3×40 ml) and the combined, dried organic layers were evaporated to give a residue. This was added to solid I, treated with ethanol (30 ml) and the mixture heated to reflux to effect solution. The solution was mixed with silica gel (Merck 7734), and the mixture evaporated. The resultant solid was purified by FCC eluting with a gradient of System A (967:30:3→945:50:5) to give the crude title compound (175 mg). This was crystallised from ethanol (0.75 ml) and washed with ether (5 ml) to give the title compound as fine white crystals.

T.l.c. System A (945:50:5), Rf 0.17. n.m.r. ($D_6$-DMSO) $\delta$2.27 (3H,s), 2.37 (3H,s), 2.43–2.60 (7H(+DMSO), m+s), 3.02 (4H,m), 3.81 (3H,s), 6.95 (1H,d), 7.32–7.45 (6H,d+s), 7.5 (1H,dd), 7.87 (1H,dd), 7.92 (1H,d), 10.1 (1H,br.s).

EXAMPLE 22

N-[4-Methoxy-3-(4-methyl-1-piperazinyl)phenyl]-2-methyl-4'-(1-oxopentyl)-[1,1'-biphenyl]-4-carboxamide A solution of sodium carbonate (111 mg) in water (5 ml), followed by tetrakis(triphenylphosphine)palladium (0) (24 mg), was added to a mixture of 1-(4-bromophenyl)pentanone (125 mg), Intermediate 10 (200 mg) and DME (10 ml) and the stirred mixture heated at reflux under nitrogen for 16 h. The cooled mixture was evaporated, treated with water (20 ml), and extracted with ethyl acetate (5×60 ml). The combined, dried organic extracts were evaporated and the residue purified by SPC eluting with System A (967:30:3) to give the title compound as a cream-coloured foam (73 mg), m.p. 65°–67°.

T.l.c. System A (945:50:5), Rf 0.16.

EXAMPLE 23

4'-Cyano-N-[4-methoxy-3-(4-methyl-1-piperazinyl)-phenyl]-2'-methyl-[1,1'-biphenyl]-4-carboxamide A mixture of Intermediate 24 (220 mg), Intermediate 11 (250 mg), sodium carbonate (292 mg) and tetrakis(triphenylphosphine)palladium (0) (19 mg) in (1:1) aqueous DME (20 ml) was heated to reflux under nitrogen for 18 h. The mixture was allowed to cool, and silica gel (5 g) was added. The solvents were evaporated and the residue chromatographed on silica gel (Merck 9385) eluting with system A (200:8:1) to give the title compound as an off-white foam (166 mg).

T.l.c. System A(100:8:1) Rf=0.51 Mass Spec. Found [MH]+ =441.

EXAMPLE 24

4-[4-(Dimethylamino)sulphonyl]phenyl]-N-[4-methoxy-3-(4'methyl-1-piperazinyl)phenyl]-3-methylbenzamide A mixture of Intermediate 10 (200 mg), 4-bromo-N,N-dimethylbenzenesulphonamide (185 mg), DME (8 ml), aqueous sodium carbonate (2N, 2 ml) and tetrakis(triphenylphosphine)palladium (0) (20 mg) was refluxed for 3 h under nitrogen. The mixture was added to water (50 ml) and extracted with dichloromethane (3×70 ml). The dried extract was evaporated and the residue was purified on a column of silica (Merck 9385) eluted with System B (485:15:1) followed by (240:10:1) to give the title compound as a white solid (155 mg) m.p. 176°–177°.

T.l.c. System B (240:10:1) Rf 0.3.

Similarly prepared were:

EXAMPLE 25

4'-(Dimethylamino)-N-[4-methoxy-3-(4-methyl-1-piperazinyl)phenyl]-2'-methyl-[1,1'-biphenyl]-4-carboxamide as a white solid (125 mg).

T.l.c. System B (90:10:1), Rf 0.5 Analysis Found: C,72.9; H,7.6; N,11.8 $C_{28}H_{34}N_4O_2$ requires C,73.3; H,7.5; N,12.2%

From a mixture of Intermediate 11 (200 mg), Intermediate 25 (120 mg), tetrakis(triphenylphosphine)palladium (0) (10 mg), aqueous sodium carbonate (2N; 2 ml) and DME (8 ml).

EXAMPLE 26

2-Chloro-N'-[4-methoxy-3-(4-methyl-1-piperazinyl)-phenyl]-N,N-dimethyl-[1,1'-biphenyl]-4,4'-dicarboxamide as a white powder (180 mg) .m.p. 203°–205° C.

T.l.c. System B (90:10:1) Rf=0.5

From a mixture of Intermediate 11 (220 mg), Intermediate 27 (200 mg), aqueous sodium carbonate (2N; 2 ml), DME (8 ml) and tetrakis (triphenylphosphine)palladium (0) (15 mg).

EXAMPLE 27

4'-(N-Acetyl-N-methylamino)-N-[4-methoxy-3-(4-methyl-1-piperazinyl)phenyl]-2'-methyl-[1,1'-biphenyl]-4-carboxamide as a white solid (160 mg) m.p. 204°–206° C.

Analysis found: C,70.5; H,7.1; N.11.0; $C_{29}H_{34}N_4O_3.0.4H_2O$ requires C,70.5; H,7.1; N.11.3%;

From a mixture of Intermediate 11 (220 mg), N-(4-bromo-3-methylphenyl)-N-methylacetamide (145 mg), tetrakis(triphenylphosphine) palladium (0) (10 mg) aqueous sodium carbonate (2N; 2 ml) and DME (8 ml).

EXAMPLE 28

N-(2-Methoxyethyl)-N'-[4-methoxy-3-(4-methyl-1-piperazinyl)phenyl]-2,N-dimethyl-[1,1'-biphenyl]-4,4'-dicarboxamide Intermediate 29 (140 mg) was added to a solution of Intermediate 11 (200 mg), sodium carbonate (114 mg), tetrakis(triphenylphosphine) palladium (0) (80 mg) in DME (12 ml) and water (6 ml) and stirred under nitrogen at reflux for 7 h. The mixture was evaporated, treated with water (20 ml) and the residue extracted with ethyl acetate (4×50 ml). The combined, dried organic extracts were purified by FCC eluting with System A (945:50:5) to give the title compound (120 mg) as a yellow foam.

T.l.c. System B (240:10:1) Rf=0.2 Assay Found: C,68.7; H,7.1; N,10.1; $C_{30}H_{36}N_4O_4.0.615H_2O$ requires C,68.3; H,7.1; N,10.1% Water Assay Found: $H_2O$ 2.1% =0.615 mol Similarly prepared were:

EXAMPLE 29

4'Acetyl-N'-[4'methoxy-3-(4'methyl-1-piperazinyl)-phenyl]-2'-methyl-[1,1'-biphenyl]-4-carboxamide as a yellow foam (30 mg).

T.l.c System B (70:8:1) Rf=0.7 n.m.r. ($CDCl_3$) $\delta$2.28 (3H,s), 2.4 (3H,s), 2.5 (4H,m), 3.04 (4H,m), 3.83 (3H,s), 6.97 (1H,d), 7.4–7.55 (3H,m), 7.58 (2H,½AA'BB'), 7.93 (1H,dd), 7.98 (1h, br.s), 8.1 (2H, ½AA'BB'), 10.2 (1H, br.s).

From a mixture of 1-(4-bromo-3-methylphenyl)ethanone (115 mg), Intermediate 11 (200 mg), sodium carbonate (114 mg), tetrakis(triphenylphosphine)palladium (0) (80 mg) and DME (12 ml).

EXAMPLE 30

N-[4-Methoxy-3-(4-methyl-1-piperazinyl)phenyl]-2'-methyl-4'-(4-morpholinylcarbonyl)-[1,1'-biphenyl]-4-carboxamide as a white solid (171 mg) m.p. 125°–130° C. (dec).

Analysis Found: C,69.7; H,7.2; N,9.9; $C_{31}H_{36}N_4O_4.0.25(CH_3CH_2)_2O.0.17H_2O$ requires C,69.85; H,7.1; N,10.2% Water assay Found: $H_2O$, 0.58% w/w≡0.17 mol From a stirred mixture of Intermediate 30 (192 mg), Intermediate 11 (250 mg), sodium carbonate (144 mg), tetrakis(triphenylphosphine) palladium (0) (31 mg), water (7 ml) and DME (14 ml).

Examples 31–36 were prepared according to the method of Example 12. Purification by FCC utilised System A (200:8:1) as eluant except where stated otherwise.

EXAMPLE 31

N-[4-Fluoro-3-(4-methyl-1-piperazinyl)phenyl]-2-methyl-4'-(methylsulphinyl)[1,1'-biphenyl]4-carboxamide as a white powdery solid (166 mg)

m.p. 191°–192° C. T.l.c. System A (75:8:1) Rf=0.4.

From a mixture of 1-bromo-4-(methylsulphinyl)benzene (130 mg) in DME (8 ml) containing 2N sodium carbonate (2 ml) and tetrakis(triphenylphosphine)palladium (0) (30 mg) to which was added Intermediate 40 (250 mg).

EXAMPLE 32

4'-Acetyl-2'-methoxy-N-[4-methoxy-3-(4-methyl-1-piperazinyl) phenyl][1,1,'-biphenyl]-4-carboxamide as a yellow foam (77 mg).

T.l.c. System A (100:8:1) Rf 0.5 Analysis Found: C,69.4; H,6.5; N,8.4; $C_{28}H_{31}N_3O_4.0.5H_2O$ requires C,69.7; H,6.7; N,8.7%

From a solution of Intermediate 44 (180 mg) in DME (4 ml) containing water (1 ml), sodium carbonate (70 mg) and tetrakis(triphenylphosphine)palladium (0) (30 mg) treated with Intermediate 11 (222 mg).

EXAMPLE 33

4'-Acetyl-2'-trifluoromethyl-N-[4-methoxy-3-(4-methyl-1-piperazinyl)phenyl]-[1,1'-biphenyl]-4-carboxamide as a pale yellow solid (58 mg) m.p. 178°–179° C.

T.l.c. System A (300:8:1) Rf=0.2

From a solution of Intermediate 43 (215 mg) in DME (4 ml) containing water (1 ml) and sodium carbonate (68 mg), treated with tetrakis(triphenylphosphine)palladium (0) (20 mg) and Intermediate 11 (222 mg).

EXAMPLE 34

N-[4-Fluoro-3-(4-methyl-1-piperazinyl)phenyl]-2-methyl-4'-cyano-[1,1'-biphenyl]-4-carboxamide as a buff-coloured foam (190 mg).

T.l.c. ether:methanol (50:1) Rf=0.06. Analysis Found: C,71.15; H,5.7; N,12.5; $C_{26}H_{25}N_4OF.0.6H_2O$ requires: C,71.1; H,6.0; N,12.75%

From a solution of Intermediate 39 (250 mg) in DME (8 ml) containing 2N sodium carbonate (3 ml) and tetrakis(triphenylphosphine)palladium (0) (30 mg), treated with (4-cyanophenyl)boronic acid (108 mg)

EXAMPLE 35

N-[4-Chloro-3-(4-methyl-1-piperazinyl)phenyl]-N',N',2'-trimethyl-[1,1'-biphenyl]-4,4'-dicarboxamide as a cream-coloured solid (45 mg) m.p. 241°–242° C.

Analysis Found: C, 65.4; H, 6.1; N, 10.6 $C_{28}H_{31}ClN_4O_2.1H_2O$ Requires: C,65.9; H, 6.5; N, 10.9%

From a mixture of Intermediate 33 (160 mg) and Intermediate 36 (225 mg) in DME (6 ml), 2N sodium carbonate (2 ml) and tetrakis(triphenylphosphine)palladium (0) (30 mg).

EXAMPLE 36

N-[4-Methoxy-3-(4-methyl-1-piperazinyl)phenyl]-2-methyl-4'-(2-oxo-1-pyrrolidinyl)[1,1'-biphenyl]-4-carboxamide as a white foam (0.13 g) m.p. 78°–81° C.

Analysis Found: C, 71.0; H, 6.9; N, 10.60 $C_{30}H_{34}N_4O_3.0.5H_2O$ requires: C,71.0; H,6.95; N,11.0%

From a mixture of 1-(4-bromophenyl)-2-pyrrolidinone (0.157 g), Intermediate 10 (0.25 g), 2N sodium carbonate (3 ml), DME (8 ml) and tetrakis(triphenylphosphine)palladium (0) (10 mg). Purification by FCC was effected using System A (978:20:2) as eluant.

EXAMPLE 37

N-[4-Methoxy-3-(4-methyl-1-piperazinyl)phenyl]-N',N'-dimethyl[1,1'-biphenyl]-4,4'-dicarboxamide A mixture of Intermediate 11 (0.3 g), 4-bromo-N,N-dimethylbenzamide (0.22 g), 2N sodium carbonate (5 ml) and tetrakis(triphenylphosphine)palladium (0) (30 mg) in DME (5 ml) was heated under reflux for 18 hours. On cooling, 2N sodium carbonate (30 ml) was added and the mixture extracted with ethyl acetate (4×40 ml). The combined extracts were dried the mixture filtered and the filtrate evaporated in vacuo. The residue was purified by FCC eluting with System A (100:8:1). Evaporation of the eluate gave the title compound (66 mg) as a white solid, m.p. 213°–216° decomp.

T.l.c. System A (100:8:1) Rf 0.1
Similarly prepared was:

EXAMPLE 38

Methyl 4'-[[[4-methoxy-3-(4-methyl-1-piperazinyl)phenyl]amino]carbonyl]-2-methyl[1,1'-biphenyl]-4-carboxylate as a pale yellow foam (1.15 g).

T.l.c. System A (100:8:1) Rf=0.36.

From a mixture of Intermediate 11 (1.1 g), Intermediate 31 (0.68 g), tetrakis(triphenylphosphine)palladium (0) (50 mg) and 2N sodium carbonate (10 ml) in DME (10 ml).

EXAMPLE 39

2-Methyl-N-[4-methoxy-3-(4-methyl-1-piperazinyl)phenyl]-4'-(trifluoromethyl)-[1,1'-biphenyl]-4-carboxamide A mixture of Intermediate 10 (200 mg), Intermediate 32 (170 mg), tetrakis(triphenylphosphine)palladium (0) (10 mg), 2N sodium carbonate (1 ml), and DME (8 ml) was refluxed for 6 h. The mixture was added to sodium hydroxide solution (2N; 25 ml) and extracted with ethyl acetate (3×50 ml). The dried extract was evaporated and the residue was purified by FCC eluting with System B (240:10:1) to give a colourless gum. The gum was dissolved in ether (1 ml) which on slow evaporation gave the title compound as a white crystalline solid (40 mg), m.p. 155°–157°.

T.l.c. System B (90:10:1) Rf 0.6.

EXAMPLE 40

N-[4-Methoxy-3-(4-methyl-1-piperazinyl)phenyl]-2'methyl-4'-[(1-pyrrolidinyl)carbonyl][1,1'-biphenyl]-4-carboxamide A mixture of Intermediate 11 (800 mg), Intermediate 48 (173 mg), tetrakis(triphenylphosphine)palladium (0) (10 mg), water (2 ml), and DME (8 ml) was refluxed under nitrogen for 16 h. The cooled mixture was added to aqueous sodium hydroxide (2N; 25 ml) and extracted with dichloromethane (3×30 ml). The dried extract was evaporated and the residue was triturated with ether (3×2 ml) to give a solid. The solid was purified by FCC eluting with System B (190:10:1) to give a gum which was treated with ether (5 ml) and evaporated to give the title compound as a white solid (200 mg) m.p. 187°–188°

T.l.c. System B (90:10:1) Rf 0.5.

Similarly prepared were:

EXAMPLE 41

N-Butyl-N'-[4-methoxy-3-(4-methyl-1-piperazinyl)-phenyl]-N,2-dimethyl[1,1'-biphenyl]-4,4'-dicarboxamide as a white solid (185 mg) m.p. 187°–188° C.

T.l.c. System B (90:10:1) Rf 0.5

From a mixture of Intermediate 11 (800 mg), Intermediate 49 (181 mg), tetrakis(triphenylphosphine)palladium (0) (10 mg), water (2 ml) and DME (8 ml).

EXAMPLE 42

N-[4-Methoxy-3-(4-methyl-1-piperazinyl)phenyl]-N',N'-dipropyl[1,1'-biphenyl]-4,4'-dicarboxamide as a white solid (199 mg) m.p. 158°–159° C.

T.l.c. System B (90:10:1) Rf 0.5

From a mixture of Intermediate 11 (800 mg), 4-bromo-3-methyl-N,N-dipropylbenzamide (191 mg), tetrakis(triphenylphosphine)palladium (0) (10 mg), water (2 ml) and DME (8 ml).

EXAMPLE 43

N,N-Diethyl-N-[4-methoxy-3-(4-methyl-1-piperazinyl)-phenyl]-2-methyl[1,1'-biphenyl]-4,4'-dicarboxamide as a white solid (200 mg) m.p. 136°–137° C.

T.l.c. System B (90:10:1) Rf 0.5

From a mixture of Intermediate 11 (800 mg), 4-bromo-N,N-diethyl-3-methylbenzamide (173 mg), tetrakis(triphenylphosphine)palladium (0) (10 mg), water (2 ml) and DME (8 ml).

EXAMPLE 44

N-(1,1-Dimethylethyl)-N'-[4-methoxy-3-(4-methyl-1-piperazinyl)phenyl]-2-methyl[1,1'-biphenyl]-4,4'-dicarboxamide as a white solid (198 mg) m.p. 177°–180° C.

T.l.c. System B (90:10:1) Rf 0.5.

From a mixture of Intermediate 11 (800 mg), Intermediate 50 (177 mg), tetrakis(triphenylphosphine)palladium (0) (10 mg), water (2 ml) and DME (8 ml).

EXAMPLE 45

4'-[(1-Azetidinyl)carbonyl]-N-[4-methoxy-3-(4-methyl-1-piperazinyl)phenyl]-2'-methyl[1,1'-biphenyl]-4-carboxamide A mixture of Intermediate 11 (800 mg), Intermediate 51 (175 mg), aqueous sodium carbonate (2N; 2 ml), DME (3 ml) and tetrakis(triphenylphosphine)palladium (0) (10 mg) was refluxed under nitrogen for 4 h. The cooled mixture was added to water (15 ml) and extracted with dichloromethane (3×50 ml). The dried extract was evaporated and the residue was triturated with ether (2×5 ml) to give a solid. The solid was purified by FCC eluting with System B (190:10:1) to give a foam. This was treated with ether (2 ml) and evaporated to give the title compound as a white solid (255 mg) m.p. 167°–170° (softens 130°)

T.l.c. System B (90:10:1) Rf 0.5.

EXAMPLE 46

N-[4-Bromo-3-(4-methyl-1-piperazinyl)phenyl]-N',N',2'-trimethyl-[1,1'-biphenyl]-4,4'-dicarboxamide A suspension of Intermediate 45 (250 mg) in dry dichloromethane (4 ml) under nitrogen at 0° C., was treated with triethylamine (1 ml of a 1M solution in dichloromethane). The resulting solution was treated dropwise with ethyl chloroformate (1 ml of a 1M solution in dichloromethane) and the mixture stirred at room temperature under nitrogen for 1 hour before treating with a solution of Intermediate 47 (240 mg) in dichloromethane (1 ml). The resulting mixture was stirred under nitrogen at room temperature for 1 week. The solution was poured into 2N sodium carbonate (20 ml), the aqueous fraction extracted with dichloromethane (10 ml) and the combined extracts dried and concentrated in vacuo to give a yellow oil. This was purified by FCC eluting with System A (200:8:1) to give a yellow oil which was triturated in ether to give the title compound as a cream-coloured solid (284 mg) m.p. 227°–228° C.

Analysis Found: C,62.6; H, 5.8; N, 10.3 $C_{28}H_{31}BrN_4O_2$ requires C, 62.8; H, 5.8; N, 10.5%

The following examples illustrate pharmaceutical formulations according to the invention. The term "active ingredient" is used herein to represent a compound of formula (I).

Pharmaceutical Example 1

| Oral Tablet A | |
| --- | --- |
| Active Ingredient | 700 mg |
| Sodium starch glycollate | 10 mg |
| Microcrystalline cellulose | 50 mg |
| Magnesium stearate | 4 mg |

Sieve the active ingredient and microcrystalline cellulose through a 40 mesh screen and blend in a appropriate blender. Sieve the sodium starch glycollate and magnesium stearate through a 60 mesh screen, add to the powder blend and blend until homogeneous. Compress with appropriate punches in an automatic tablet press. The tablets may be coated with a thin polymer coat applied by the film coating techniques well known to those skilled in the art. Pigments may be incorporated in the film coat.

Pharmaceutical Example 2

| Oral Tablet B | |
| --- | --- |
| Active Ingredient | 500 mg |
| Lactose | 100 mg |
| Maize Starch | 50 mg |
| Polyvinyl pyrrolidone | 3 mg |
| Sodium starch glycollate | 10 mg |
| Magnesium stearate | 4 mg |
| Tablet Weight | 667 mg |

Sieve the active ingredient, lactose and maize starch through a 40 mesh screen and blend the powders in a suitable blender. Make an aqueous solution of the polyvinyl pyrrolidone (5–10% w/v). Add this solution to the blended powders and mix until granulated; pass the granulate through a 12 mesh screen and dry the granules in a suitable oven or fluid bed dryer. Sieve the remaining components through a 60 mesh screen and blend them with the dried granules. Compress, using appropriate punches, on an automatic tablet press.

The tablets may be coated with a thin polymer coat applied by film coating techniques well known to those skilled in art. Pigments may be incorporated in the film coat.

Pharmaceutical Example 3

| Inhalation Cartridge | |
|---|---|
| Active Ingredient | 1 mg |
| Lactose | 24 mg |

Blend active ingredient, particle size reduced to a very fine particle size (weight mean diameter ca. 5 μm) with the lactose in a suitable powder blender and fill the powder blender into No. 3 hard gelatin capsules.

The contents of the cartridges may be administered using a powder inhaler.

Pharmaceutical Example 4

| Injection Formulation | % w/v |
|---|---|
| Active ingredient | 1.00 |
| Water for injections B.P. to | 100.00 | sodium chloride may be added to adjust the tonicity of the solution and the pH may be adjusted to that of maximum stability and/or to facilitate solution of the active ingredient using dilute acid or alkali or by the addition of suitable buffer salts. Antioxidants and metal chelating salts may also be included.

The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

We claim:

1. A compound of formula (I):

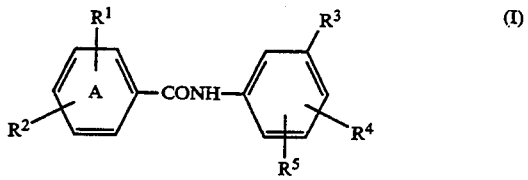

or a physiologically acceptable salt or solvate thereof wherein $R^1$ represents a halogen or hydrogen atom or a $C_{1-6}$alkyl or $C_{1-6}$alkoxy group;

$R^2$ represents a phenyl group optionally substituted by one or two substituents selected from a halogen atom, $C_{1-6}$alkyl, hydroxy$C_{1-6}$alkyl, $C_{1-6}$alkoxy, hydroxy, —CF$_3$, —CN, —NO$_2$, —CO$_2$R$^{10}$, —COR$^6$, —SR$^6$, —SOR$^6$, —SO$_2$R$^6$, —CR$^6$=NOR$^7$, —CONR$^6$R$^7$, CONR$^6$(CH$_2$)$_m$CO$_2$R$^7$, —CONR$^6$(CH$_2$)$_m$OC$_{1-4}$alkyl, —SO$_2$NR$^6$R$^7$, —OC(O)NR$^6$R$^7$, —(CH$_2$)$_n$NR$^8$R$^9$, —(CH$_2$)$_n$OC(O)C$_{1-4}$alkyl or a C$_{1-4}$alkoxyalkyl group optionally substituted by a C$_{1-4}$alkoxy or hydroxy group;

$R^3$ represents the group

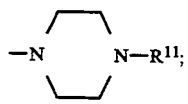

$R^4$ and $R^5$, which may be the same or different, each independently represent a hydrogen atom or a halogen atom, or a group selected from hydroxy, $C_{1-6}$alkoxy or $C_{1-6}$alkyl;

$R^6$, $R^7$ and $R^8$, which may be the same or different, each independently represent a hydrogen atom or a $C_{1-6}$alkyl group;

or —NR$^6$R$^7$ forms a saturated heterocyclic ring selected from pyrrolidino, piperidino, morpholino or thiomorpholino;

$R^9$ represents a hydrogen atom or a group selected from $C_{1-6}$alkyl, —COR$^{12}$ or —SO$_2$R$^{13}$;

or —NR$^8$R$^9$ forms a saturated heterocyclic ring selected from pyrrolidino, piperidino, morpholino, thiomorpholino, 2-oxo-1-pyrrolidino, 4-oxo-3-thiazolidino or 2-oxo-tetrahydro-1,3-thiazino;

$R^{10}$ represents a hydrogen atom or a $C_{1-6}$alkyl group optionally substituted by one or two substituents selected from a $C_{1-6}$alkyl group, $C_{1-6}$alkoxy group, hydroxy or —NR$^6$R$^7$;

$R^{11}$ represents a hydrogen atom or a $C_{1-6}$alkyl group;

$R^{12}$ represents a hydrogen atom or a group selected from $C_{1-6}$alkyl, $C_{1-6}$alkoxy or a $C_{1-4}$ alkoxyalkyl group;

$R^{13}$ represents a $C_{1-6}$alkyl or phenyl group;

m represents an integer from 1 to 3; and n represents zero or an integer from 1 to 3.

2. A compound of formula (I):

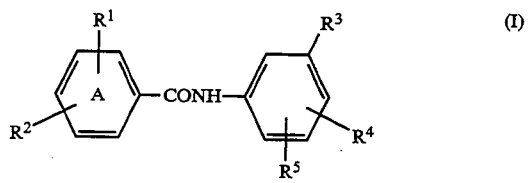

or a physiologically acceptable salt or solvate thereof wherein $R^1$ represents a halogen or hydrogen atom or a $C_{1-6}$alkyl or $C_{1-6}$alkoxy group;

$R^2$ represents a phenyl group optionally substituted by one or two substituents selected from a halogen atom, $C_{1-6}$alkyl, hydroxy$C_{1-6}$alkyl, $C_{1-6}$alkoxy, hydroxy, —CN, —NO$_2$, —CO$_2$R$^{10}$, —COR$^6$, —SR$^6$, —SOR$^6$, —SO$_2$R$^6$, —CR$^6$=NOR$^7$, —CONR$^6$R$^7$, —CONR$^6$(CH$_2$)$_m$CO$_2$R$^7$, —CONR$^6$(CH$_2$)$_m$OC$_{1-4}$alkyl, —SO$_2$NR$^6$R$^7$, —OC(O)NR$^6$R$^7$, —(CH$_2$)$_n$NR$^8$R$^9$, —(CH$_2$)$_n$OC(O)C$_{1-4}$alkyl or a C$_{1-4}$alkoxyalkyl group optionally substituted by a C$_{1-4}$alkoxy or hydroxy group;

$R^3$ represents the group

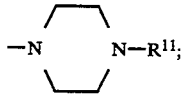

$R^4$ and $R^5$, which may be the same or different, each independently represent a hydrogen atom or a halogen atom, or a group selected from hydroxy, $C_{1-6}$alkoxy or $C_{1-6}$alkyl;

$R^6$, $R^7$ and $R^8$, which may be the same or different, each independently represent a hydrogen atom or a $C_{1-6}$alkyl group;

or —NR$^6$R$^7$ forms a saturated heterocyclic ring selected from pyrrolidino, piperidino, morpholino or thiomorpholino;

R⁹ represents a hydrogen atom or a group selected from $C_{1-6}$alkyl, —COR¹² or —SO₂R¹³;
or —NR⁸R⁹ forms a saturated heterocyclic ring selected from pyrrolidino, piperidino, morpholino or thiomorpholino;
R¹⁰ represents a hydrogen atom or a $C_{1-6}$alkyl group optionally substituted by one or two substituents selected from a $C_{1-6}$alkyl group, $C_{1-6}$alkoxy group, hydroxy or —NR⁶R⁷;
R¹¹ represents a hydrogen atom or a $C_{1-6}$alkyl group;
R¹² represents a hydrogen atom or a group selected from $C_{1-6}$alkyl, $C_{1-6}$alkoxy or a $C_{1-4}$alkoxyalkyl group;
R¹³ represents a $C_{1-6}$alkyl or phenyl group;
m represents an integer from 1 to 3; and
n represents zero or an integer from 1 to 3.

3. A compound according to claim 1 wherein the group R² is attached in the meta or para position of the benzene ring A relative to the amide linkage.

4. A compound according to claim 1 wherein R² represents a phenyl group substituted by a single atom or group in a position para to the bond to the phenyl ring A in general formula (I).

5. A compound according to claim 1 wherein R² represents a phenyl group substituted by two atoms or groups wherein one substituent is attached to the position para to the bond to the phenyl ring A in general formula (I) and the second substituent is attached in a position ortho to the bond to the phenyl ring A in general formula (I).

6. A compound according to claim 1 wherein R² represents a phenyl group substituted by a group selected from hydroxymethyl, hydroxy, —COCH₃, —SOCH₃, —C(CH₃)═NOH, —CON(CH₃)₂, —SO₂NH₂, —SO₂NHCH₃, —SO₂N(CH₃)₂, —OC(O)N(CH₃)₂, —NHCH₃, —N(CH₃)₂, —N(CH₃)COCH₃, —CH₂NHCO₂CH₂CH₃, —CH₂N(CH₃)COCH₂OCH₃, —NHSO₂CH₃,

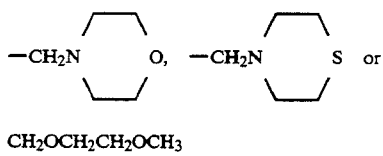

CH₂OCH₂CH₂OCH₃ and optionally further substituted by a chlorine atom or a methyl group.

7. A compound according to claim 1 wherein R¹ represents a hydrogen atom or a $C_{1-6}$alkyl group.

8. A compound according to claim 1 wherein R⁴ is attached at the para-position relative to the amide linkage.

9. A compound according to claim 1 wherein R⁴ represents a halogen atom, or a hydroxy or $C_{1-6}$alkoxy group.

10. A compound according to claim 1 wherein R⁵ is a hydrogen atom.

11. A compound according to claim 1 wherein R⁵ is a halogen atom.

12. A compound according to claim 1 wherein R¹¹ is a $C_{1-6}$alkyl group.

13. A compound of formula (I)

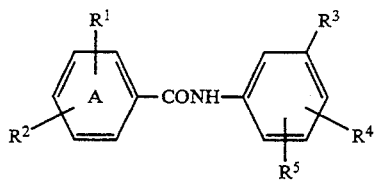

or a physiologically acceptable salt or solvate thereof wherein
R¹ represents a hydrogen atom or a $C_{1-6}$alkyl group;
R² represents a phenyl group optionally substituted by one or two substituents selected from a halogen atom, $C_{1-6}$alkyl, hydroxy$C_{1-6}$alkyl, $C_{1-6}$alkoxy, hydroxy, —CF₃, —CN, —CO₂R¹⁰, —COR⁶, —SR⁶, SOR⁶, —CR⁶═NOR⁷, —CONR⁶R⁷, —CONR⁶(CH₂)$_m$OC$_{1-4}$alkyl, —SO₂NR⁶R⁷, —OC(O)NR⁶R⁷, —(CH₂)$_n$NR⁸R⁹, or a $C_{1-4}$alkoxyalkyl group optionally substituted by a $C_{1-4}$alkoxy group;
R³ represents the group

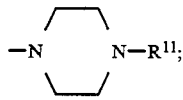

R⁴ and R⁵, which may be the same or different, each independently represent a hydrogen atom or a halogen atom, or a $C_{1-6}$alkoxy group;
R⁶, R⁷ and R⁸, which may be the same or different, each independently represent a hydrogen atom or a $C_{1-6}$alkyl group;
or —NR⁶R⁷ forms a saturated heterocyclic ring selected from pyrrolidino, piperidino, morpholino or thiomorpholino;
R⁹ represents a hydrogen atom or a group selected from $C_{1-6}$alkyl, —COR¹² or —SO₂R¹³; or —NR⁸R⁹ forms a saturated heterocyclic ring selected from pyrrolidino, piperidino, morpholino, thiomorpholino, 2-oxo-1-pyrrolidino, 4-oxo-3-thiazolidino or 2-oxo-tetrahydro-1,3-thiazino;
R¹⁰ represents a $C_{1-6}$alkyl group;
R¹¹ represents a $C_{1-6}$alkyl group;
R¹² represents a group selected from $C_{1-6}$alkyl, $C_{1-6}$alkoxy or a $C_{1-4}$alkoxyalkyl group;
R¹³ represents a $C_{1-6}$alkyl group; and
n represents zero or 1.

14. A compound according to claim 3 wherein R² is attached in the para-position of the benzene ring A relative to the amide linkage.

15. A compound according to claim 1 wherein R² represents a phenyl group optionally substituted by one or two substituents selected from a halogen atom or a $C_{1-6}$alkyl group; hydroxymethyl; hydroxy; —CN; —COR⁶ where R⁶ is a $C_{1-6}$alkyl group; —SR⁶ where R⁶ is a $C_{1-6}$alkyl group; —CR⁶═NOR⁷ where R⁶ is a hydrogen atom or a $C_{1-6}$alkyl group and R⁷ is a hydrogen atom or a $C_{1-6}$alkyl group; —COR⁶R⁷ where R⁶ and R⁷ each independently represent $C_{1-6}$alkyl groups or —NR⁶R⁷ forms a saturated heterocyclic group selected from piperidino, morpholino or thiomorpholino; —CONR⁶(CH₂)$_n$OC$_{1-4}$alkyl where R⁶ is a $C_{1-6}$alkyl group and n is two; —SO₂NR⁶R⁷ where R⁶ and R⁷ each independently represent a hydrogen atom or a $C_{1-6}$alkyl group; —OC(O)NR⁶R⁷ where R⁶ and R⁷ each independently represent a $C_{1-6}$alkyl group; —$(CH_2)_nR^8R^9$ where $R^8$ is a hydrogen atom or a $C_{1-6}$alkyl group, $R^9$ is a $C_{1-6}$alkyl group or —$COR^{12}$ (where $R^{12}$ is a $C_{1-6}$alkyl group, a $C_{1-6}$alkoxy group or a $C_{1-4}$alkoxyalkyl group) or —$SO_2R^{13}$ (where $R^{13}$ is a $C_{1-6}$alkyl group), or —$NR^8R^9$ forms a saturated heterocyclic group selected from piperidino, morpholino or thiomorpholino, and n is zero, 1 or 2; or a $C_{1-4}$alkoxyalkyl group substituted by a $C_{1-4}$alkoxy group.

16. A compound according to claim 15 wherein $R^2$ represents a phenyl group optionally substituted by one or two substituents selected from a halogen atom; or a methyl group; hydroxymethyl; hydroxy; —CN; —$COR^6$ where $R^6$ is a methyl, ethyl, propyl or butyl group; —$SCH_3$; —$SOCH_3$; —$CR^6$=$NOR^7$ where $R^6$ is a hydrogen atom or a methyl group and $R^7$ is a hydrogen atom or a methyl group; —$CON(CH_3)_2$; —$CONR^6R^7$ where —$NR^6R^7$ forms a morpholino ring; $CON(CH_3)(CH_2)_2OC_{1-4}$alkyl; —$SO_2NR^6R^7$ where $R^6$ and $R^7$ each independently represent a hydrogen atom or a methyl group; $OC(O)N(CH_3)_2$; —$(CH_2)_nNR^8R^9$ where $R^8$ is a hydrogen atom or a methyl group, $R^9$ is a methyl group or —$COCH_3$, —$CO_2CH_3$, —$COCH_2OCH_3$, or —$SO_2CH_3$, or —$NR^8R^9$ forms a morpholino or thiomorpholino ring and n is zero, 1 or 2; or a methoxymethyl group substituted by a methoxy group.

17. A compound according to claim 7 wherein $R^1$ represents a methyl group.

18. A compound according to claim 9 wherein $R^4$ represents a fluorine or chlorine atom or a hydroxy or methoxy group.

19. A compound according to claim 11 wherein $R^5$ represents a chlorine or fluorine atom.

20. A compound according to claim 12 wherein $R^{11}$ represents a methyl group.

21. A compound selected from:

4'-[(2-methoxyethoxy)methyl]-N-[4-methoxy-3-(4-methyl-1-piperazinyl)phenyl]-2'-methyl-[1,1'-biphenyl]-4-carboxamide;

4'-cyano-N-[4-methoxy-3-(4-methyl-1-piperazinyl)phenyl]-2'-methyl-[1,1'-biphenyl]-4-carboxamide;

N-[4-methoxy-3-(4-methyl-1-piperazinyl)phenyl]-N',N',2'-trimethyl-[1,1'-biphenyl]-4,4'-dicarboxamide;

4'-(dimethylamino)-N-[4-methoxy-3-(4-methyl-1-piperazinyl)phenyl]-2'-methyl-[1,1'-biphenyl]-4-carboxamide;

2-chloro-N'-[4-methoxy-3-(4-methyl-1-piperazinyl)phenyl]-N,N-dimethyl-[1,1'-biphenyl]-4,4'-dicarboxamide;

N-[4-chloro-3-(4-methyl-1-piperazinyl)phenyl]-N',N',2'-trimethyl-[1,1'-biphenyl]-4,4'-dicarboxamide;

N-(1,1-dimethylethyl)-N'-[4-methoxy-3-(4-methyl-1-piperazinyl) phenyl]-2-methyl[1,1'-biphenyl]-4,4'-dicarboxamide;

4'-[(1-azetidinyl)carbonyl]-N-[4-methoxy-3-(4-methyl-1-piperazinyl) phenyl]-2'-methyl[1,1'-biphenyl]-4-carboxamide;

4'-acetyl-2'-trifluoromethyl-N-[4-methoxy-3-(4-methyl-1-piperazinyl)phenyl]-[1,1'-biphenyl]-4-carboxamide;

N-[4-bromo-3-(4-methyl-1-piperazinyl)phenyl]-N',N',2'-trimethyl-[1,1'-biphenyl]-4,4'-dicarboxamide;

4'-hydroxy-N-[4-methoxy-3-(4-methyl-1-piperazinyl)phenyl]-[1,1'-biphenyl]-4-carboxamide;

4'-acetyl-N-[4-methoxy-3-(4-methyl-1-piperazinyl)phenyl]-2'-methyl-[1,1'-biphenyl]-4-carboxamide;

N-[4-methoxy-3-(4-methyl-1-piperazinyl)phenyl]-2'-methyl-4'-(4-morpholinylcarbonyl)-[1,1'-biphenyl]-4-carboxamide;

4'-acetyl-2'-methoxy-N-[4-methoxy-3-(4-methyl-1-piperazinyl) phenyl][1,1'-biphenyl]-4-carboxamide;

N-[4-methoxy-3-(4-methyl-1-piperazinyl)phenyl]-N',N'-dimethyl[1,1'-biphenyl]-4,4'-dicarboxamide;

N-[4-methoxy-3-(4-methyl-1-piperazinyl)phenyl]-2'methyl-4'-[(1-pyrrolidinyl)carbonyl][1,1'-biphenyl]-4-carboxamide;

N,N-diethyl-N-[4-methoxy-3-(4-methyl-1-piperazinyl)phenyl]-2-methyl[1,1'-biphenyl]-4,4'-dicarboxamide;

N-[4-methoxy-3-(4-methyl-1-piperazinyl)phenyl]-2'-methyl-4'-[(methylsulphonyl)amino]-[1,1'-biphenyl]-4-carboxamide;

N-butyl-N'-[4-methoxy-3-(4-methyl-1-piperazinyl)phenyl]-N,2-dimethyl[1,1'-biphenyl]-4,4'-dicarboxamide;

N-[4-methoxy-3-(4-methyl-1-piperazinyl)phenyl]-N',N'-dipropyl[1,1'-biphenyl]-4,4'-dicarboxamide;

N-[4-methoxy-3-(4-methyl-1-piperazinyl)phenyl]-2-methyl-4'-(methylsulphinyl)-[1,1'-biphenyl]-4-carboxamide;

4'-acetyl-N-[4-methoxy-3-(4-methyl-1-piperazinyl)phenyl]-2-methyl-[1,1'-biphenyl]-4-carboxamide;

N-[4-methoxy-3-(4-methyl-1-piperazinyl)phenyl]-2'-methyl-4'-methylamino-[1,1'-biphenyl]-4-carboxamide;

ethyl [4'-[[[4-methoxy-[3-(4-methyl-1-piperazinyl)]-phenyl]amino]carbonyl]-2-methyl-([1,1'-biphenyl]-4-yl)]methyl carbamate;

4'-[[[4-methoxy-3-(4-methyl-1-piperazinyl)phenyl-]amino]carbonyl]-2'-methyl-[1,1'-biphenyl]-4-dimethylcarbamate;

4'-[[(methoxyacetyl)methylamino]methyl]-N-[4-methoxy-3-(4-methyl-1-piperazinyl)phenyl]-2'-methyl-[1,1'-biphenyl]-4-carboxamide;

or a physiologically acceptable salt or solvate thereof.

22. A pharmaceutical composition comprising an effective amount of at least one compound of formula (I) as defined in claim 1 or a physiologically acceptable salt or solvate thereof, together with at least one physiologically acceptable carrier or excipient.

* * * * *